United States Patent [19]

Beard et al.

[11] 4,002,640
[45] * Jan. 11, 1977

[54] 5(6)-BENZENE RING SUBSTITUTED BENZIMIDAZOLE-2-CARBAMATE DERIVATIVES HAVING ANTHELMINTIC ACTIVITY

[75] Inventors: Colin C. Beard, Palo Alto; John A. Edwards, Los Altos; John H. Fried, Palo Alto, all of Calif.

[73] Assignee: SYNTEX (U.S.A.) Inc., Palo Alto, Calif.

[ * ] Notice: The portion of the term of this patent subsequent to Dec. 30, 1992, has been disclaimed.

[22] Filed: Nov. 3, 1975

[21] Appl. No.: 628,434

Related U.S. Application Data

[60] Division of Ser. No. 417,963, Nov. 21, 1973, Pat. No. 3,929,821, which is a continuation-in-part of Ser. No. 319,299, Dec. 29, 1972, abandoned.

[52] U.S. Cl. .......................... 260/309.2
[51] Int. Cl.$^2$ ...................... C07D 235/32
[58] Field of Search ................ 260/309.2

[56] References Cited

UNITED STATES PATENTS

| | | | |
|---|---|---|---|
| 3,682,952 | 8/1972 | Actor et al. | 260/309.2 |
| 3,929,821 | 12/1975 | Beard et al. | 260/309.2 |
| 3,929,824 | 12/1975 | Beard et al. | 260/309.2 |

FOREIGN PATENTS OR APPLICATIONS

| | | | |
|---|---|---|---|
| 809,234 | 6/1974 | Belgium | 260/309.2 |

*Primary Examiner*—Natalie Trousoe
*Attorney, Agent, or Firm*—Joseph I. Hirsch; William B. Walker

[57] ABSTRACT

Benzene ring substituted benzimidazole-2-carbamate derivatives represented by the formula:

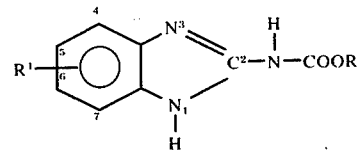

where R is a lower alkyl group having 1 to 4 carbon atoms; $R^1$ is $-SOR^2$, $-SO_2R^2$, $-SCN$, $-SR^5$, $-OR^5$ or $M'(CH_2)_nMR^7$ where M and M' are independently O, S,

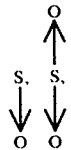

$R^7$ is lower alkyl having 1 to 4 carbon atoms, or aryl, and $n$ is 1–4; $R^2$ is lower alkyl having from 1 to 6 carbon atoms, cycloalkyl having 3 to 7 carbon atoms, lower alkenyl or lower alkynyl having 3 to 6 carbon atoms, or aralkyl or aryl; and $R^5$ is lower alkenyl, lower alkynyl, or aralkyl. The $R^1$ substitution is at the 5(6)-position.

The compounds are useful as pesticides, particularly as anthelmintic and antifungal agents.

15 Claims, No Drawings

5(6)-BENZENE RING SUBSTITUTED BENZIMIDAZOLE-2-CARBAMATE DERIVATIVES HAVING ANTHELMINTIC ACTIVITY

REFERENCE TO PARENT APPLICATIONS

This application is a division of application Ser. No. 417,963, filed Nov. 21, 1973 now U.S. Pat. No. 3,929,827, which, in turn, is a continuation-in-part application of application Ser. No. 319,299, filed Dec. 29, 1972, now abandoned

FIELD OF THE INVENTION

This invention relates to novel chemical compounds. More particularly, this invention relates to novel anthelmintically active benzimidazole-2-carbamate derivatives wherein the benzene ring is substituted at the 5(6)-position.

BACKGROUND OF THE INVENTION

Anthelmintically active benzimidazole-2-carbamate derivatives either unsubstituted at the 5(6)-position or substituted with different substituents than those described and claimed herein are known in this art (for example, see U.S. Pat. Nos. 3,480,642; 3,573,321; 3,574,845; 3,578,676; and 3,595,870). Related fungicidal compounds are also shown in U.S. Pat. Nos. 2,933,504 and 3,010,968.

SUMMARY OF THE INVENTION

The novel benzene ring substituted benzimidazole-2-carbamate derivatives of the present invention can be represented by the following formula:

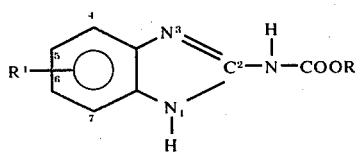

where R is a lower alkyl group having 1 to 4 carbon atoms; $R^1$ is $-SOR^2$, $-SO_2R^2$, $-SCN$, $-SR^5$, $-OR^5$ or $M'(CH_2)_nMR^7$ where M and M' are independently O, S,

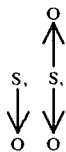

$R^7$ is lower alkyl having 1 to 4 carbon atoms or aryl, and $n$ is 1–4; $R^2$ is a lower alkyl having from 1 to 6 carbon atoms, cycloalkyl having 3 to 7 carbon atoms, lower alkenyl or lower alkynyl having 3 to 6 carbon atoms, or aralkyl or aryl; and $R^5$ is lower alkenyl, lower alkynyl or aralkyl. The $R^1$ substitution is at the 5(6)-position.

The hydrogen on the nitrogen at the 1-position can be replaced with substituents which do not adversely affect the anthelmintic and/or antifungal properties of the basic compound, including N-alkylcarbamoyl, N,N-dialkylcarbamoyl, N-alkoxycarbonylcarbamoyl, cyano, trichloromethylthio, alkylthio, phenylthio, nitrophenylthio, alkylsulfinyl, phenylsulfinyl, acyl, alkoxycarbonyl, benzoyl, alkoxycarbonylalkylcarbonyl, alkyl, alkenyl, benzyl, alkoxyalkyl, alkoxycarbonylalkyl, carboxyalkyl, hydroxy, and conventional esters and ethers thereof, etc.

As used in this specification and claims, the term "lower alkyl" refers to both straight and branched chain alkyl groups having either a total of from 1 through 4 carbon atoms or from 1 through 6 carbon atoms, and thus includes primary, secondary and tertiary alkyl groups. Typical lower alkyls include, for example, methyl, ethyl, n-propyl, isopropyl, n-butyl, isobutyl, t-butyl, n-amyl, n-hexyl and the like. The term "cycloalkyl" refers to cyclic hydrocarbon groups having from 3 to 7 carbon atoms such as, for example, cyclopropyl, cyclopentyl, cyclohexyl, and the like. The term "lower alkenyl" refers to an unsaturated hydrocarbon group having from 3 to 6 carbon atoms and a single carbon-carbon double bond, provided that the double bond cannot be on the α-carbon atoms. Typical alkenyl groups include, for example, 2-propenyl, 2-butenyl, 3-butenyl, and the like. The term "lower alkynyl" refers to an unsaturated hydrocarbon group having from 3 to 6 carbon atoms, and a single carbon-carbon triple bond, provided also that the triple bond cannot be on the α-carbon atom. Typical alkynyl groups include, for example, 2-propynyl, 2-butynyl, 3-butynyl, and the like. An alkyl, alkenyl or alkynyl group of the $R^1$ moiety can be optionally substituted with one or more radicals, for example, thiocyanato; alkoxy, such as methoxy; aryl, such as phenyl; aroyl, such as benzoyl; hydroxy; cycloalkyl; halo; cyano; or nitro radicals. The term "alkoxy" refers to the group having the formula RO- wherein R is a lower alkyl as defined above. Typical alkoxy groups include, for example, methoxy, ethoxy, t-butoxy and the like. The term "halo" refers to iodo, bromo, chloro and fluoro groups. The term "aryl" refers to an aromatic hydrocarbon group, such as phenyl. The term "aralkyl" refers to an aryl substituted alkyl group, such as, for example, benzyl or phenethyl. The term "aroyl" refers to the group having the formula

where R' is an aryl group. The aryl or aralkyl groups can be optionally substituted with one or more lower alkyl, alkoxy, halo, nitro, cyano, thiocyanato, isothiocyanato, trifluoromethyl, alkylthio, alkylsulfinyl, alkysulfonyl, acyl or acylamino where the acyl portion has 1 to 6 carbon atoms, $-SO_2NR^3R^4$ or $-N(R^3)SO_2R^4$ radicals; where $R^3$ and $R^4$ are independently hydrogen or lower alkyl having 1 to 6 carbon atoms. The terms "alkylthio", "alkylsulfinyl", and "alkylsulfonyl" refer to those groups having the formula RS-,

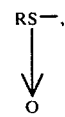

and

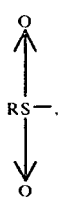

respectively, where R is a lower alkyl (1–6C) as defined above. The term "acyl" refers to acyl groups derived from carboxylic acids having 1 through 6 carbon atoms such as acetyl, propionyl, butyryl, valeryl, isovaleryl, hexanoyl and the like.

The compounds of the present invention, and the nontoxic salts thereof formed with pharmaceutically acceptable inorganic or organic acids, possess broad spectrum activity against parasites of mammals, including both mature and immature parasitic forms, as represented for example, by the genera Trichostronglylus, Haemonchus, Ostertagia, Cooperia, Nematodirus, and Stronglyoides, and specifically, for example against *Nematospiroides dubius*, *Hymenolepis Nana*, *Syphacia obvelata*, and/or *Aspiculuris tetraptera*. In particular, these compounds are found to exhibit high activity against various helminthic infections of the intestinal tract of economically important animals, coupled with lower systemic toxicity to the host animal.

The compounds of the present invention are also useful as antifungal agents, particularly as systemic fungicides for controlling fungal diseases of plants of economic importance.

In addition to the stated anthelminthic and antifungal properties, certain compounds of the present invention are also useful as intermediates in the preparation of further compounds of this invention. For example, the 5(6)-sulfinyl compounds can be prepared and then utilized as starting materials for the preparation of the corresponding 5(6)- sulfonyl compounds.

Where the compound has a basic moiety, the term non-toxic salts as used herein refers to those pharmaceutically acceptable salts of the compounds of this invention which do not adversely affect the antifungal or anthelmintic properties of the basic compound, such as those salts conventionally used in the art. Such non-toxic salts include, for example, salts of inorganic acids such as, for example, sulfuric, sulfonic, sulfamic, nitric, phosphoric, hydrochloric acids and the like, and salts of organic acids such as, for example, acetic, citric, lactic, palmitic, tartaric, succinic, maleic, benzoic acids and the like. Where the compound has an acidic moiety, the non-toxic salts include cation salts, such as, for example, the salts of sodium, potassium, ammonium, and the like.

The amount of the compound to be administered will depend upon the actual compound utilized, and upon the weight of the animal being treated. In general, however, the daily dosage level will usually be between about 5 mg/kg and 100 mg/kg of body weight of the animal being treated. The active ingredient is adapted to be administered to the animal by mixing it with the diet of the animal, as with a feed mix, or formulating it with a non-toxic carrier to give anthelmitic compositions. The carrier may be an orally ingestible container for the active ingredient such as, for example, a gelatin capsule, or it may be an excipient of the kind normally used in medicaments of this character, including maize starch, terra alba, lactose, sucrose, calcium phosphate, gelatin, stearic acid, agar, pectin or the like. Examples of suitable liquid carriers are peanut oil, sesame oil and water.

A wide variety of pharmaceutical forms can be employed in those cases wherein the medicament is not admixed with the feed. Thus, if a solid carrier is used, the compound can be administered in tablet or capsule form. If a liquid carrier is used, the medicament may be in the form of a soft gelatin capsule or in a liquid suspension.

In general, the compounds of the present invention can be prepared from benzene starting compounds having nitro and amino or acylamino (for example, acetamido) substituents at adjacent positions on the benzene nucleus (e.g., the 1- and 2-positions), and the desired $R^1$ moiety (or a moiety which can be reacted to give the desired $R^1$ moiety) at the 4- or 5-position of the benzene nucleus (i.e., at what will be the 5- or 6-position of the benzimidazole compound to be prepared). The nitro group is reduced to an amino group to afford a benzene derivative having amino groups at the 1- and 2-positions. The diamino compound is then reacted with a 1,3-bis(alkoxy-carbonyl)-S-alkyl-isothiourea to give the corresponding 5(6)-subsituted benzimidazole 2-carbamate derivative.

The functional moiety at the 4- or 5-position of the benzene starting material can be, for example, the thiocyanato group which can be left unaltered at its position during formation of the remainder of the benzimidazole 2-carbamate, or it can be converted, by known reactions, to an alkylthio or arylthio group, which, in turn, can be converted, also by known reactions, to the alkyl- or aryl-sulfinyl or alkyl- or arylsulfonyl group. The functional moiety at the 4- or 5-position can also be chloro which can be reacted with a substitued or unsubstituted aryl mercaptan to afford the corresponding arylthio compound, which, in turn, can be converted, for example, to an arylsulfinyl compound. In this regard, the thiocyanato, chloro, etc., starting materials are compounds previously reported in the literature.

A reaction sequence exemplifying these steps and particularly adapted to produce 5(6)-alkylsulfinyl-, 5(6)-alkylsulfonyl-, and 5(6)-thiocyanato-benzimidazole 2-carbamates is as follows:

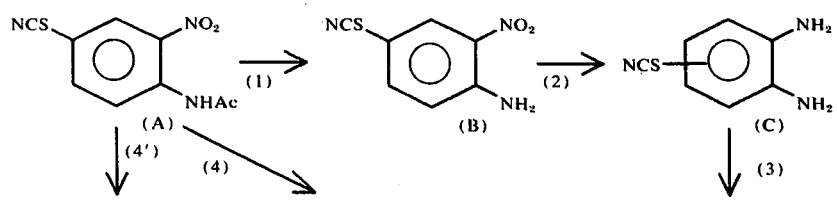

-continued
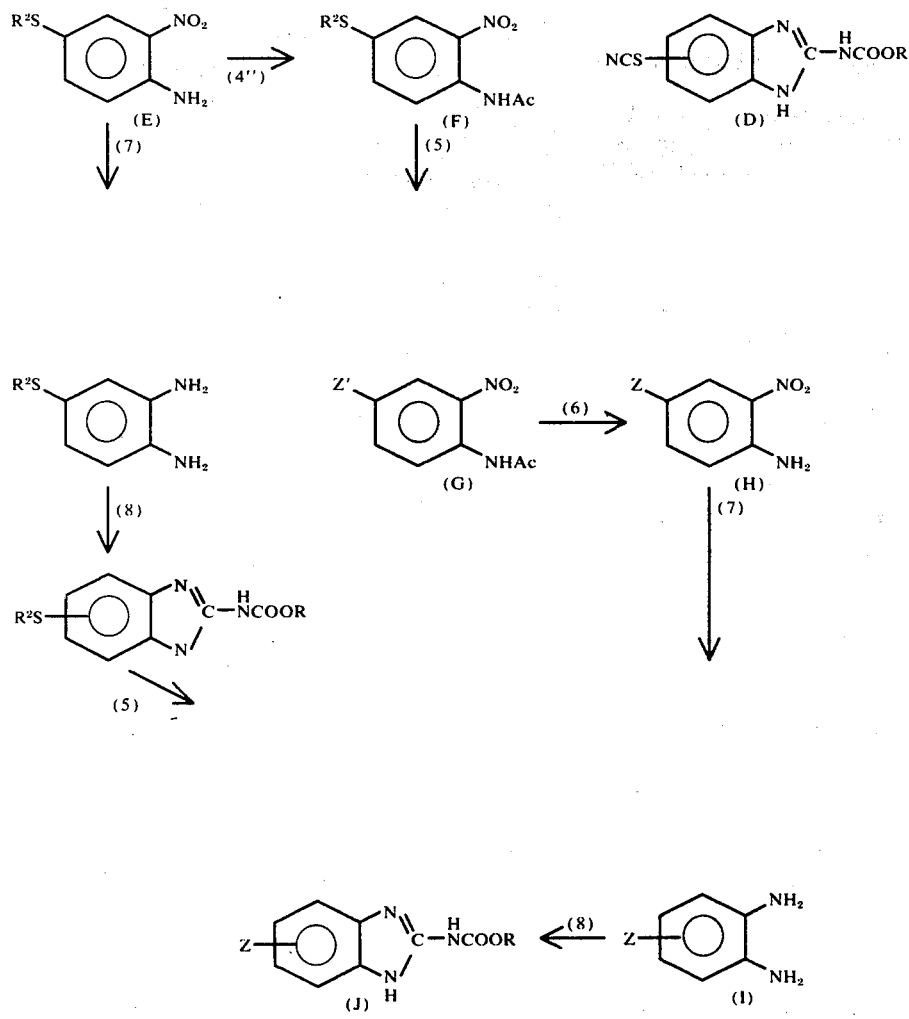
where Z, depending upon the reactants and/or reaction condition employed, represents

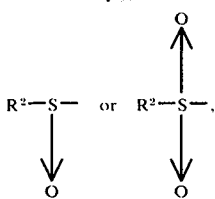

where R² is as defined above, particularly a lower alkyl having 1–6 carbon atoms.

A reaction sequence particularly useful for preparing substituted or unsubstituted 5(6)-arylthio-, arylsulfinyl- and arylsulfonyl-benzimidazole 2-carbamates is as follows:

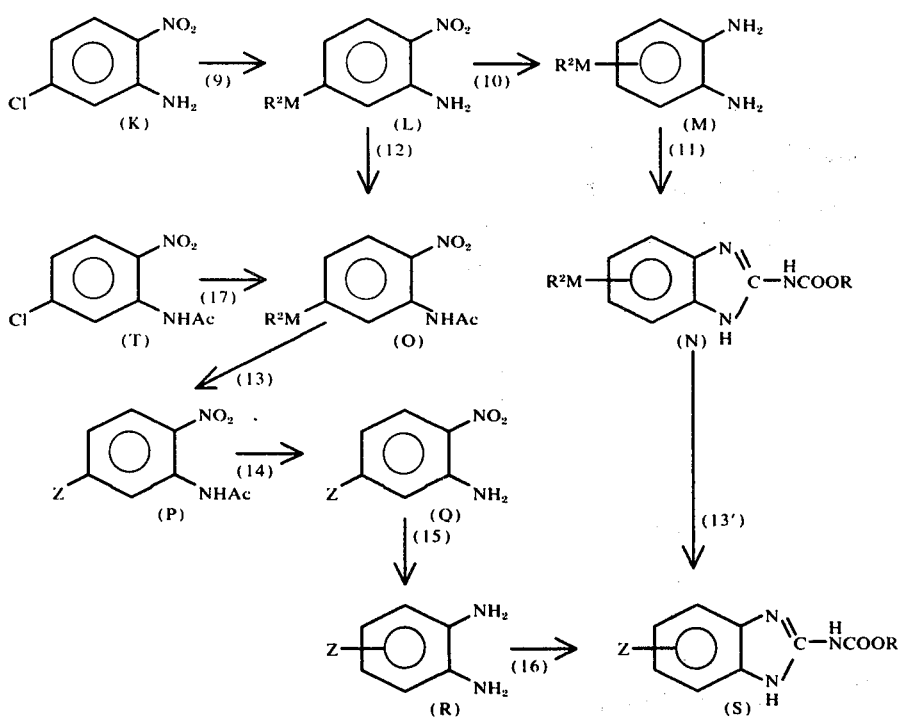

where R² is as defined above, particularly aryl, Z is

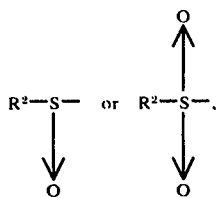

and M is either O or S.

A suitable starting material for the first reaction sequence above is 1-acetamido-2-nitro-4-thiocyanato-benzene (i.e., Compound A) which can be prepared according to the method of F. Challenger and A. T. Peters, J. Chem Soc., 1364 (1928). Starting materials for the other reaction sequences include, for example, 1-amino-2-nitro-4-thiocyanato-benzene, 2-amino-4-chloro-1-nitrobenzene, 2-acetamido-4-chloro-1-nitrobenzene, 1-acetamido-4hydroxy-2 nitrobenzene and 1-amino-4-hydroxy-2 nitrobenzene.

Conversion of an acylamino group, for example, an acetamido group, to an amino group, as exemplified by steps 1, 6, and 14, above, can be effected by treating the acylamino group-containing compound with a strong acid, such as hydrochloric acid, or strong base, such as sodium hydroxide, potassium hydroxide, potassium carbonate, or sodium carbonate in aqueous methanol at about 20° to about 100° C for about ¼ hour to about 24 hours. The selection of either the strong acid or the strong base will depend upon the substituent at the 4-or 5-position of the benzene nucleus; for example, with the presence of a thiocyanato substituent, strong acid must be utilized if that substituent is to be retained. Generally for other substituents disclosed a strong base is utilized; however, the necessary material for a particular substituent or compound can be determined by routine experimentation or will be apparent from the nature and chemical stability of the particular compound involved.

Reduction of the nitro group to an amino group as exemplified by steps 2, 7, 10 and 15 above, can be effected by a variety of techniques, for example, the nitro group can be catalytically reduced utilizing hydrogen over a palladium/charcoal catalyst. This reaction is conducted in an inert solvent, such as methanol, at a temperature from about 0° to 35° C, generally about room temperature, for about ½ to about 2 hours. Other suitable inert solvents include ethyl acetate, acetic acid, and ethanol. This technique is particularly suitable for compounds which contain a arylsulfinyl or arylsulfonyl substituent at the 4-or 5-position of the benzene nucleus.

Another suitable reducing technique is to treat the nitro-containing compound with iron powder and a ferrous salt, such as ferrous sulfate or ferrous chloride, in aqueous methanol at reflux under neutral conditions for about 1 to about 6 hours. Other suitable reaction media include acetic acid or concentrated hydrochloric acid, and other suitable metals, such as zinc. It is desirable to add the iron powder in distinct portions (as opposed to all at one time), and to carefully monitor the reactants and reaction conditions to insure, for example, that sulfinyl compounds are not reduced to the corresponding thio compounds. This technique is suitable for materials which contain a arylthio or arylsulfonyl substituent.

A reduction technique suitable for use with thiocyanato or arylthio substituted compounds is to treat such compounds with stannous chloride in concentrated hydrochloric acid at a temperature in a range from about −20° to about 100° C, generally about room temperature, for about ½ to about 6 hours. An excess of the stannous chloride reactant should be utilized, generally about 5 parts (by weight) per unit weight of the starting compound.

The reduction can also be conducted using sodium dithionite (sodium hydrosulfite) in basic aqueous methanol at reflux for 10 minutes − 6 hours.

The diamino compounds, as exemplified by Compounds C, I, M, and R above are converted to the corresponding benzimidazole 2-carbamate compounds, for example by reaction steps 3, 8, 11 and 16 respectively, by reacting the diamino compound with a 1/3-bis(alkoxycarbonyl)-S-alkyl isothiourea, for example 1,3-bis (methoxycarbonyl)-S-methyl isothiourea or 1,3-bis(ethoxycarbonyl)-S-methyl isothiourea, in an aqueous alcoholic medium, for example, aq. methanol or aq. ethanol, at from about room temperature to the reflux temperature of the reaction medium for about ½ to about 6 hours. The reaction medium is preferably made acidic to a pH of about 4–6 with, for example, a sufficient amount (e.g., 1–2 moles) of acetic acid. About 1–2 moles, generally about 1.1 moles, of the isothiourea reactant are utilized per mole of the diamino compound.

Conversion of the thiocyanato group of the 1-acetamido-2-nitro-4-thiocyanatobenzene starting material to an alkylthio or arylthio group, simultaneous with the conversion of the acetamido group to an amino group, as represented by step (4') above, can be effected by treating the thiocyanato compound (e.g., compound A) with an alkylhalide, a cycloalkylhalide, or an activated aryl halide, in dimethylformamide or an alcoholic medium, such as methanol or ethanol, in the presence of base, such as potassium hydroxide, sodium hydroxide, potassium carbonate, or sodium carbonate, The reaction is conducted at a temperature from about 10° to about 50° C, generally at about room temperature, for about ¼ to about 12 hours using essentially a molar ratio of the principal reactants. Where the hydrocarbon radical of the halide reactant is dissimilar to the hydrocarbon radical of the alcoholic reaction medium, the reaction is preferably conducted in isopropanol or dimethylformamide. Optionally, the thiocyanato group can be converted to the alkylthio or arylthio group, without change in the acetamido group, as exemplified by step (4) above, by treatment of the 1-acetamido-2-nitro-4-thiocyanatobenzene starting material, at room temperature, with sodium borohydride in dimethylformamide, for about ¼ to about 2 hours, followed by treatment with one of the aforementioned halide reactants under the conditions as set forth above.

The conversion of an amino group to an acylamino group, for example, an acetamido group, as exemplified by steps 4" and 12 above, can be conveniently effected by treatment with an acyl halide, for example acetyl chloride or acetic anhydride, in an inert organic reaction medium which dissolves, or is adjusted to dissolve, the compound being treated. For example, suitable organic reaction media include tetrahydrofuran in the presence of pyridine, acetone in the presence of base such as potassium hydroxide or potassium carbonate, or pyridine alone. Acetic anhydride can be used as the acylating reactant and can also be utilized as the reaction medium. When so utilized, the acetic anhydride is present in substantial excess, generally in an amount sufficient to dissolve the compound being reacted. The well-known Schotten-Baumann reaction can also be utilized for the above purposes. In such a reaction, the compound being treated is dissolved in an aqueous base, an excess of acetic anhydride is added and the precipitated product collected by filtration. When acetic anhydride is utilized in these reactions, it can be utilized in combinations with an acidic catalyst, such as sulfuric acid or paratoluene-sulfonic acid. These reactions are typically conducted at a temperature from about −30° C to about room temperature for about ¼ hour to about 24 hours using a slight excess (about 1.5–2 moles) of the acylating agent.

Conversion of the alkylthio or arylthio group to the corresponding sulfinyl or sulfonyl group, or conversion of the sulfinyl to the sulfonyl group, as exemplified by steps 5, 13 and 13' above, is conveniently effected by treatment with a peracid, such as peracetic acid, perbenzoic acid, metachloroperbenzoic acid, or perphthalic acid, in an inert solvent for the compound being treated. Suitable solvent materials include, for example, methylene chloride or chloroform. If the compound being treated is not soluble in the particular reaction media desired to be utilized, then a co-solvent material, such as acetic acid or methanol, should be utilized in an amount sufficient to dissolve the compound being treated. Typically, the reaction is conducted at a temperature from about −30° C to about room temperature for about ½ hour to about 6 hours. When it is desired to convert the alkylthio or arylthio group to the corresponding sulfinyl group, molar quantities are utilized, and reaction conditions are carefully monitored to insure that the reaction does not proceed further than desired. When it is desired to convert the alkylthio or arylthio group to the corresponding sulfonyl group, or it is desired to convert the sulfinyl group to the corresponding sulfonyl group, an excess of the peracid material, for example, 2 moles of the peracid per mole of the compound being treated, is utilized and the reaction conditions do not have to be as carefully monitored. Optionally, such conversions can also be effected by treatment with periodate in aqueous methanol or aqueous acetonitrile at a temperature in the range of about −20° to about 50° C., for about ½ to about 12 hours.

When 2-amino-4-chloro-1-nitrobenzene (ie, compound K) or 2-acetamido-4-chloro-1-nitrobenzene is utilized as a starting material, it can be converted to the corresponding substituted or unsubstituted 4-phenylthio compound, as represented by reaction 9 above, by the reaction thereof with an appropriate aryl mercaptan, such as phenylmercaptan, p-chlorophenylmercaptan or p-methoxyphenylmercaptan, in an inert solvent, such as dimethylformamide, ethanol, or methanol, in the presence of a suitable inorganic base, such as potassium hydroxide, potassium carbonate, sodium carbonate, sodium hydroxide or sodium hydride. Typically, this reaction is conducted at a temperature from about 20° to about 150° C (i.e., to about the reflux temperature of the solvent material) for about ½ to about 6 hours, using a slight excess (1.5–2 moles) of the mercaptan reactant. Reaction step 17 above can be conducted as described above with respect to step 9; however, the reaction is preferably conducted in dimethylformide using, eg. 2-acetamido-4-chloro-1-nitrobenzene (ie, compound T) as the starting material. The 2-amino-4-chloro-1-nitrobenzene starting material can also be converted to the corresponding 4-arylsulfonyl compound by displacement of the chlorine with metal arylsulfinate, for example, sodium benzene sulfinate. This displacement is typically conducted in an inert, polar organic solvent, such as dimethylformamide, acetone, or dimethylsulfoxide, at a temperature from about room temperature to the reflux temperature of the particular solvent employed for about ½ to about 6 hours, using essentially a molar ratio of the starting material and the metal sulfinate.

Compounds having the $-OR^5$ or $-O(CH_2)_nMR^7$ substituent at the 5(6)-position can be prepared by reacting 1-acetamido-4-hydroxy-2-nitrobenzene with a lower alkenyl halide (such as 1-bromoprop-2-ene), a lower alkynyl halide (such as 1-bromo-prop-2-yne), an aralkyl halide (such as benzyl bromide), a haloalkyl aryl ether (such as 2-bromoethyl phenyl ether), a haloalkyl alkyl sulfide (such as chloromethyl methyl sulfide), or a haloalkyl alkyl ether (such as chloromethyl methyl ether), etc., and then conducting other steps, as necessary and as set forth above, to give the desired compound. Compounds having the $-S(CH_2)_nMR^7$ substituent at the 5(6)-position can be prepared by treating 1-acetamido-2-nitro-4-thiocyanato-benzene, at room temperature with sodium borohydride in dimethylformamide for about ¼ to about 2 hours, followed by treatment with a haloalkyl alkyl sulfide (such as chloromethyl methyl sulfide), a haloalkyl alkyl ether (such as chloromethyl methyl ether), a haloalkyl aryl sulfide (such as chloromethyl p-chlorophenyl sulfide), etc., and then conducting other steps, as necessary and as set forth above, to give the desired compound. The thio bridges in the $-M'(CH_2)_nMR^7$ substituents can be converted to the corresponding sulfinyl and/or sulfonyl bridges by the steps set forth above.

In each of the process steps, described herein above and below, unless otherwise indicated, the respective intermediate products are preferably separated from the reaction mixture and purified prior to their use as starting materials for the next step in the process. Such separation and purification can be effected by any suitable procedure. For example, typical separation procedures include filtration, extraction, evaporation, and typical purification procedures include crystallization, and both thin-layer and column chromatography. Optimum separation and isolation procedures can be obtained for any given step by routine experimentation as will be apparent to those skilled in this art.

Particular compounds falling within the scope of the present invention can be prepared by selecting an appropriate starting material, for example, from those referred to above, and then selecting particular reaction step or steps, as for example described above, to give the compound desired. In view of this disclosure, the preparation of particular compounds, including compounds falling within the scope of the present invention but not particularly described in this specification, will be apparent to those skilled in this art.

Exemplary of the compounds of the present invention, as represented by the structural formula above, are the following illustrative compounds:
5(6)-ethylsulfinyl-2-carbomethoxyaminobenzimidazole;
5(6)-n-propylsulfinyl-2-carbomethoxyaminobenzimidazole;
5(6)-n-butylsulfinyl-2-carbomethoxyaminobenzimidazole;
5(6)-phenylsulfinyl-2-carbomethoxyaminobenzimidazole;
5(6)-p-fluorophenylsulfinyl-2-carbomethoxyaminobenzimidazole;
5(6)-naphth-2'-ylsulfinyl-2-carbomethoxyaminobenzimidazole;
5(6)-methylthiomethylthio-2-carbomethoxyaminobenzimidazole;
5(6)-methoxymethylthio-2-carbomethoxyaminobenzimidazole;
5(6)-methoxymethoxy-2-carbomethoxyaminobenzimidazole;
5(6)-methylthiomethoxy-2-carbomethoxyaminobenzimidazole;
5(6)-methoxymethylsulfinyl-2-carbomethoxyaminobenzimidazole;
5(6)-methylsulfinylmethoxy-2-carbomethoxyaminobenzimidazole;
5(6)-trifluoromethylmethylsulfinyl-2-carbomethoxyaminobenzimidazole;
5(6)-(prop-2-en-1-ylthio)-2-carbomethoxyaminobenzimidazole;
5(6)-(prop-2-en-1-ylsulfinyl)-2-carbomethoxyaminobenzimidazole;
5(6)-(prop-2-yn-1-ylthio)-2-carbomethoxyaminobenzimidazole;
5(6)-(prop-2-yn-1-ylsulfinyl)-2-carbomethoxyaminobenzimidazole;

These compounds are presently preferred since they have shown substantial activity against the helminths specifically referred to above.

Other illustrative compounds falling within the scope of the present invention include, for example:
5(6)-n-hexylsulfinyl-2-carbomethoxyaminobenzimidazole;
5(6)-methylsulfonyl-2-carbomethoxyaminobenzimidazole;
5(6)-ethylsulfonyl-2-carbomethoxyaminobenzimidazole;
5(6)-n-propylsulfonyl-2-carbomethoxyaminobenzimidazole;
5(6)-i-propylsulfonyl-2-carbomethoxyaminobenzimidazole;
5(6)-n-butylsulfonyl-2-carbomethoxyaminobenzimidazole;
5(6)-n-hexylsulfonyl-2-carbomethoxyaminobenzimidazole;
5(6)-phenylsulfonyl-2-carbomethoxyaminobenzimidazole;
5(6)-p-chlorophenylsulfinyl-2-carbomethoxyaminobenzimidazole;
5(6)-m-chlorophenylsulfinyl-2-carbomethoxyaminobenzimidazole;
5(6)-p-methylphenylsulfinyl-2-carbomethoxyaminobenzimidazole;
5(6)-p-methoxyphenylsulfinyl-2-carbomethoxyaminobenzimidazole;
5(6)-m-methoxyphenylsulfinyl-2-carbomethoxyaminobenzimidazole;

5(6)-cyanomethylsulfinyl-2-carbomethoxyaminobenzimidazole;
5(6)-phenethylthio-2-carbomethoxyaminobenzimidazole;
5(6)-phenethylsulfinyl-2-carbomethoxyaminobenzimidazole;
5(6)-trichloromethylmethylsulfinyl-2-carbomethoxyaminobenzimidazole;
5(6)-tribromomethylmethylsulfinyl-2-carbomethoxyaminobenzimidazole;
5(6)-trifluoromethylthiomethylthio-2-carbomethoxyaminobenzimidazole;
5(6)-trichloromethylthiomethylthio-2-carbomethoxyaminobenzimidazole;
5(6)-trifluoromethylthiomethoxy-2-carbomethoxyaminobenzimidazole;
5(6)-methoxyethylthio-2-carbomethoxyaminobenzimidazole;
5(6)-methoxyethylsulfinyl-2-carbomethoxyaminobenzimidazole;
5(6)-ethoxyethylthio-2-carbomethoxyaminobenzimidazole;
5(6)-ethoxyethylsulfinyl-2-carbomethoxyaminobenzimidazole;
5(6)-methoxyethoxy-2-carbomethoxyaminobenzimidazole;
5(6)-ethoxyethoxy-2-carbomethoxyaminobenzimidazole;
5(6)-ethoxymethylthio-2-carbomethoxyaminobenzimidazole;
5(6)-ethoxymethylsulfinyl-2-carbomethoxyaminobenzimidazole;
5(6)-methylthioethylthio-2-carbomethoxyaminobenzimidazole;
5(6)-methylsulfinylethylthio-2-carbomethoxyaminobenzimidazole;
5(6)-methylthioethoxy-2-carbomethoxyaminobenzimidazole;
5(6)-methylsulfinylethoxy-2-carbomethoxyaminobenzimidazole;
5(6)-methylsulfinylmethylthio-2-carbomethoxyaminobenzimidazole;
5(6)-thiocyanatomethylsulfinyl-2-carbomethoxyaminobenzimidazole;
5(6)-(2,2,3,3-tetrafluoroprop-1-ylsulfinyl)-2-carbomethoxyaminobenzimidazole;
5(6)-(2,2,3,3,3-pentafluoroprop-1-ylsulfinyl)-2-carbomethoxyaminobenzimidazole;
5(6)-phenoxyethoxy-2-carbomethoxyaminobenzimidazole;
5(6)-phenoxyethylthio-2-carbomethoxyaminobenzimidazole;
5(6)-phenoxyethylsulfinyl-2-carbomethoxyaminobenzimidazole;
5(6)-(p-chlorophenylthiomethylthio)-2-carbomethoxyaminobenzimidazole;
5(6)-phenylsulfinylmethylthio-2-carbomethoxyaminobenzimidazole;
5(6)-(2,2-dimethoxyethylthio)-2-carbomethoxyaminobenzimidazole;
5(6)-methylthiomethylthio-2-carbomethoxyaminobenzimidazole;
5(6)-(β-hydroxyphenethylthio)-2-carbomethoxyaminobenzimidazole;
5(6)-(β-hydroxyphenethylsulfinyl)-2-carbomethoxyaminobenzimidazole;
5(6)-cyclopropylmethylsulfinyl-2-carbomethoxyaminobenzimidazole;
5(6)-cyclopentylsulfinyl-2-carbomethoxyaminobenzimidazole;
5(6)-cyclohexylsulfinyl-2-carbomethoxyaminobenzimidazole;
5(6)-benzylsulfinyl-2-carbomethoxyaminobenzimidazole;
5(6)-p-nitrophenylsulfinyl-2-carbomethoxyaminobenzimidazole;
5(6)-p-cyanophenylsulfinyl-2-carbomethoxyaminobenzimidazole;
5(6)-(2-cyanoethylsulfinyl)-2-carbomethoxyaminobenzimidazole;
5(6)-p-acetamidophenylsulfinyl-2-carbomethoxyaminobenzimidazole;
5(6)-p-sulfamoylphenylsulfinyl-2-carbomethoxyaminobenzimidazole;
5(6)-p-sulfonylaminophenylsulfinyl-2-carbomethoxyaminobenzimidazole;
5(6)-p-methylthiophenylsulfinyl-2-carbomethoxyaminobenzimidazole;
5(6)-p-trifluoromethylphenylsulfinyl-2-carbomethoxyaminobenzimidazole;
5(6)-[p-(n-propylsulfinyl)phenylsulfinyl]-2-carbomethoxyaminobenzimidazole;
5(6)-[p-(n-butylsulfonyl)phenylsulfinyl]-2-carbomethoxyaminobenzimidazole;
5(6)-thiocyanato-2-carbomethoxyaminobenzimidazole;

and the corresponding 2-carbethoxyamino-, 2-carbopropoxyamino-, and 2-carbobutoxyamino- compounds.

DESCRIPTION OF SPECIFIC EMBODIMENTS

The following specific description is given to enable those skilled in this art to more clearly understand and practice the present invention. It should not be considered as a limitation upon the scope of the invention but merely as being illustrative and representative thereof.

PREPARATION 1

175 G. of S-methyl isothiouronium sulfate in one liter of water is cooled to 0° C and 162.5 g. of methylchloroformate added, followed by the addition of a solution of 250 g. potassium hydroxide in 750 ml. water at 0° to 5° C. The crude product is extracted into benzene, the benzene dried and evaporated, and the residue recrystallized from methanol. 1,3-bis(methoxycarbonyl)-S-methyl isothiourea is thus obtained.

In a similar manner, substituting ethylchloroformate, propylchloroformate and butylchloroformate for the methylchloroformate, 1,3-bis(ethoxycarbonyl)-S-methyl isothiourea, 1,3-bis(propoxycarbonyl)-S-methyl isothiourea, and 1,3-bis(butoxycarbonyl)-S-methyl isothiourea are, respectively, prepared.

EXAMPLE I 2G. of 1-amino-2-nitro-4-thiocyanatobenzene is mixed with 6ml. of concentrated hydrochloric acid and the mixture cooled to about −40° C. A solution of 12 g. stannous chloride in 6 ml. concentrated hydrochloric acid is added dropwise and the mixture allowed to warm slowly to room temperature. After 15–20 minutes at 15°–20° C, the product is filtered off and washed with 12 ml. 6N hydrochloric acid. Treatment with 25 ml. of saturated potassium bicarbonate solution and extraction with chloroform gives the free base. Recrystallization from benzene yields 1,2-diamino-4-thiocyanatobenzene.

A solution of 1.3 g. 1,2-diamino-4-thiocyanatobenzene and 1.7 g. 1,3-bis(methoxycarbonyl)-S-methyl isothiourea in 20 ml. ethanol and 20 ml. water is treated with 0.5 ml. acetic acid. The mixture is refluxed for 1 ½ hours, then cooled and filtered. The solid is recrystallized from methanol-chloroform to yield 5(6)-thiocyanato-2-carbomethoxyaminobenzimidazole (m.pt. 270° dec.).

In a similar manner substituting
1,3-bis(ethoxycarbonyl)-S-methyl isothiourea,
1,3-bis(propoxycarbonyl)-S-methyl isothiourea, and
1,3-bis(butoxycarbonyl)-S-methyl isothiourea for the
1,3-bis(methoxycarbonyl)-S-methyl isothiourea,
5(6)-thiocyanato-2-carbethoxyaminobenzimidazole,
5(6)-thiocyanato-2-carbopropoxyaminobenzimidazole, and
5(6)-thiocyanato-2-carbobutoxyaminobenzimidazole
are prepared, respectively.

EXAMPLE II 5G. of 1-acetamido-2-nitro-4-thiocyanatobenzene in 70 ml. of n-propyl alcohol containing 4.8 g. potassium hydroxide is treated with 2.6 g. n-propylbromide. The mixture is stirred overnight at 15°–20° C., then poured into water, and extracted with chloroform. The dried extracts are stripped under vacuum and the residual red oil is dissolved in 25 ml. of acetic anhydride. A few drops of sulfuric acid are added and the mixture left at 20°–25° C for 1 hour. Sodium acetate is added and the solvent removed under vacuum. The residue is treated with water and the crude product filtered off. Recrystallization from methanol gives 1-acetamido-2-nitro-4-n-propylthiobenzene. (This intermediate may also be obtained directly by alkylation of 1-acetamido-2-nitro-4-thiocyanatobenzene with n-propylbromide in dimethylformamide in the presence of sodium borohydride.)

3.81 G. of 1-acetamido-2-nitro-4-n-propylthiobenzene in 35 ml. chloroform is treated at −20° to −15° C with a solution of 3.0 g. 40% peracetic acid in 3 ml. methanol. The mixture is allowed to warm to 20° C and stirred at 15°–25° C for four hours, then washed with sodium bisulfite solution and sodium bicarbonate solution. Removal of the chloroform leaves a gum which is treated on a steam bath, with 15 ml. 5N sodium hydroxide for one hour. The mixture is cooled, extracted with chloroform, separated and the solvent removed. The crude residue is recrystallized from benzene yielding 1-amino-2-nitro-4-n-propylsulfinylbenzene.

1.14 G. of 1-amino-2-nitro-4-n-propylsulfinylbenzene is hydrogenated in 100 ml. methanol at 1 atmosphere pressure, in the presence of 1 g. of 5% palladized carbon, until the theoretical uptake of hydrogen has occurred. The catalyst is removed by filtration and the filtrate evaporated. The residual gum is treated with 1.2 g. 1,3-bis-methoxycarbonyl-S-methyl isothiourea and 0.3 ml. acetic acid in a boiling mixture of 10 ml. ethanol and 10 ml. water. After three hours the mixture is cooled, filtered and 5(6)-n-propylsulfinyl-2-carbomethoxyaminobenzimidazole is recrystallized from ethanol.

In a similar manner substituting methyl iodide, ethyl iodide, i-propyl bromide, butyl bromide, i-butyl bromide, pentyl bromide, hexyl bromide, cyclopropyl bromide, cyclopentyl bromide, and cyclophexyl bromide for the n-propyl bromide, the corresponding 1-amino-2-nitro-4-alkylsulfinylbenzene, 1-amino-2-nitro-4-cycloalkylsulfinylbenzene, 5(6)-alkylsulfinyl-2-carbomethoxyaminobenzimidazole, and 5(6)-cycloalkylsulfinyl-2-carbomethoxyaminobenzimidazole compounds are prepared, including
5(6)-methylsulfinyl-2-carbomethoxyaminobenzimidazole;
5(6)-ethylsulfinyl-2-carbomethoxyaminobenzimidazole;
5(6)-i-propylsulfinyl-2-carbomethoxyaminobenzimidazole; and
5(6)-n-butylsulfinyl-2-carbomethoxyaminobenzimidazole.

By reacting the 1-amino-2-nitro-4-alkylsulfinylbenzene and 1-amino-2-nitro-4-cycloalkylsulfinylbenzene compounds so prepared with 1,3-bis(methoxycarbonyl)-S-methyl isothiourea, 1,3-bis(ethoxycarbonyl)-S-methyl isothiourea, 1,3-bis (propoxycarbonyl)-S-methyl isothiourea, or 1,3-bis(butoxycarbonyl)-S-methyl isothiourea, the corresponding 5(6)-alkylsulfinyl-2-carbalkoxyaminobenzimidazole and 5(6)-cycloalkylsulfinyl-2-carbalkoxyaminobenzimidazole compounds are prepared where R is methyl, ethyl, propyl or butyl.

EXAMPLE III

5 G. of 1-acetamido-2-nitro-4-thiocyanatobenzene and 1.7 ml. of methyl iodide are added to a solution of 4.8 g. of potassium hydroxide in 70 ml. of ethanol. The mixture is left overnight at room temperature, then diluted with water. 1-Amino-2-nitro-4-methylthiobenzene is collected by filtration.

A few drops of concentrated sulfuric acid are added to a solution of 3.7 g. of 1-amino-2-nitro-4-methylthiobenzene in 37 ml. of acetic anhydride. The mixture is left at room temperature for 1-2 hours, then treated with a slight excess of sodium acetate and evaporated. Water is added and 1-acetamido-2-nitro-4-methylthiobenzene is collected by filtration.

4.0 G. of 1-acetamido-2-nitro-4-methylthiobenzene is treated in 40 ml. chloroform with 12 ml. 40% peracetic acid at room temperature. The mixture is left for 1½ hours, then the product is filtered off and washed with methanol, yielding 1-acetamido-4-methylsulfonyl-2-nitrobenzene.

4 G. of 1-acetamido-4-methylsulfonyl-2-nitrobenzene is treated with 40 ml. concentrated hydrochloric acid on the steam bath for 1 hour. The mixture is cooled and diluted with water. 1-Amino-4-methylsulfonyl-2-nitrobenzene is collected by filtration.

2 G. of 1-amino-4-methylsulfonyl-2-nitrobenzene is treated in 200 ml. methanol with hydrogen at 4 atmospheres pressure in the presence of Raney nickel catalyst. The catalyst is removed by filtration and the filtrate concentrated to yield 1,2-diamino-4-methylsulfonylbenzene.

0.5 G. 1,2-diamino-4-methylsulfonylbenzene and 0.6 g. 1,3-bis-(methoxycarbonyl)-S-methyl isothiourea and 0.2 ml. acetic acid are heated at reflux in 10 ml. ethanol and 10 ml. water for four hours. The mixture is cooled, filtered and the product recrystallized from methanol-chloroform yielding 5(6)-methylsulfonyl-2-carbomethoxyaminobenzimidazole (m.pt. about 270° C. dec.).

In a similar manner, using ethyl iodide, propyl bromide, butyl bromide, pentyl bromide, hexyl bromide, cyclopentyl bromide or cyclohexyl bromide in place of the methyl iodide, the corresponding 1,2-diamino-4-alkylthiobenzene, 1,2-diamino-4-cycloalkylthiobenzene, 5(6)-alkylsulfonyl-2-carbomethoxyaminobenzimidazole, and 5(6)-cycloalkylsulfonyl-2-carbomethoxyaminobenzimidazole compounds are prepared.

In a similar manner reacting the 1,2-diamino compounds so prepared with 1,3-bis-ethoxycarbonyl-S-methyl isothiourea, 1,3-bis-propoxycarbonyl-S-methyl isothiourea, or 1,3-bis-butoxycarbonyl-S-methyl isothiourea instead of 1,3 -bis-methoxycarbonyl-S-methyl isothiourea, the corresponding 5(6)-alkylsulfonyl-2-carbalkoxyaminobenzimidazole and 5(6)-cycloalkylsulfonyl-2-carbalkoxyaminobenzimidazole compounds are prepared, where R is either ethyl, propyl or butyl.

EXAMPLE IV 5.85 G. of 1-amino-2-nitro-4-thiocyanatobenzene in 20 ml. dimethylformamide is treated under nitrogen with 1.14 g. sodium borohydride at not greater than 30° C. The mixture is stirred for one hour at 15°–20° C, then treated with 5 ml. of propargyl bromide at 20°–20° C. After a further 3 hours, water is added and the crude product extracted with chloroform. The dried chloroform solution is passed through a column of silica gel to remove a little polar material. Pure 1-amino-2-nitro-4-(prop-2-yn-1-ylthio)benzene is obtained from the eluate.

4.8 G. of 1-amino-2-nitro-4-(prop-2-yn-1-ylthio)benzene in 14 ml. concentrated hydrochloric acid is treated with a solution of 24 g. stannous chloride in 14 ml. concentrated hydrochloric acid at 20°–30° C. After about 30 minutes, the mixture is neutralized with a saturated solution of potassium bicarbonate and chloroform added. The mixture is filtered, the chloroform layer separated, dried and evaporated yielding 1,2-diamino-4-(prop-2-yn-1-ylthio)benzene.

4.0 G. of 1,2-diamino-4-(prop-2-yn-1-ylthio)benzene in 25ml. ethanol and 25 ml. water is treated with 4.9 g. 1,3-bis-methoxycarbonyl-S-methyl isothiourea and 1.5 ml. acetic acid, at reflux, for 3 hours. The mixture is cooled and 5(6)-(prop-2-yn-1-ylthio)-2-carbomethoxyaminobenzimidazole isolated by filtration. Recrystallization may be effected from methanol-chloroform.

1.31 G. of 5(6)-(prop-2-yn-1-ylthio)-2-carbomethoxyaminobenzimidazole is dissolved in a mixture of 65 ml. acetic acid and 65 ml. chloroform. A solution of 1.02 g. m-chloroperbenzoic acid in 20 ml. chloroform is added at −20° to −15° C. The mixture is allowed to warm slowly to 20° C and left for 5 hours. The solvents are removed under vacuum and the residue treated with sodium bicarbonate solution. 5(6)-(prop-2-yn-1-ylsulfinyl)-2-carbomethoxyaminobenzimidazole is filtered off, and may be recrystallized from methanol-chloroform.

In a similar manner using 2-propenyl bromide, 2-butenyl bromide, 3-butenyl bromide, 2-pentenyl bromide, 2-hexenyl bromide, 2-butynyl bromide, 3-butynyl bromide, 2-pentynyl bromide, or 2-hexynyl bromide in place of the propargyl bromide, the corresponding 5(6)-alkenylthio-, 5(6)-alkynylthio-, 5(6)-alkenylsulfinyl-, and 5(6)-alkynylsulfinyl-2-carbomethoxyaminobenzimidazole compounds are prepared, including 5(6)-(prop-2-en-1-ylthio)-2-carbomethoxyaminobenzimidazole, and 5(6)-(prop-2-en-1-ylsulfinyl)-2-carbomethoxyaminobenzimidazole.

In a similar mannner using the 1,2-diamino-4-alkenylthiobenzene or 1,2-diamino-4-alkynylthiobenzene compounds prepared above in this Example and substituting 1,3-bis-ethoxycarbonyl-S-methyl isothiourea, 1,3-bis-propoxycarbonyl-S-methyl isothiourea, or 1,3-bis-butoxycarbonyl-S-methyl isothiourea for the 1,3-bis-methoxycarbonyl-S-methylisothiourea, the corresponding 5(6)-alkenylthio-, 5(6)-alkynylthio-, 5(6)-alkenylsulfinyl- or 5(6)-alkynylsulfinyl-2-carbalkoxyaminobenzimidazole compounds are prepared where R is either ethyl, propyl or butyl.

EXAMPLE V

The 5(6)-alkenylthio-2-carbalkoxyaminobenzimidazoles and 5(6)-alkynylthio-2-carbalkoxyaminobenzimidazoles of Example IV are treated with 2 moles of a peracid (eg, m-chloropenbenzoic acid or peracetic acid) per mole of starting material according to the procedure set forth in the third paragraph of Example III, or the fourth paragraph of Example IV (but for a longer period of time), to afford the corresponding 5(6)-alkenylsulfonyl-2-carbalkoxyaminobenzimidazole and 5(6)-alkynylsulfonyl-2-carbalkoxyaminobenzimidazole compounds. The 5(6)-alkenylsulfonyl or 5(6)-alkynylsulfonyl compounds can also be prepared in similar manner from the corresponding 5(6)-alkenylsulfinyl or 5(6)-alkynylsulfinyl compounds of Example IV.

EXAMPLE VI 1.0 g. of 1-acetamido-2-nitro-4-benzylthiobenzene, as prepared in Example VII, is treated with 2 ml. 5N sodium hydroxide and 6 ml. methanol on the steam bath for 15 minutes. The mixture is diluted with water, and the 1-amino-2-nitro-4-benzylthiobenzene filtered off.

0.9 g. of 1-amino-2-nitro-4-benzylthiobenzene in 5 ml. concentrated hydrochloric acid is treated with 4.5 g. stannous chloride very briefly on the steam bath. The mixture is cooled and the liquid decanted from the gum, which is then washed with 5ml. of cold 6N hydrochloric acid. Treatment of the gum with potassium bicarbonate solution yields 1,2-diamino-4-benzylthiobenzene which is isolated by extraction into chloroform and purified by recrystallization from cyclohexane. In similar manner to the procedure of the third paragraph of Example IV, 5(6)-benzylthio-2-carbomethoxyaminobenzimidazole is prepared.

In a similar manner substituting p-chlorobenzyl bromide, p-methylbenzyl bromide and p-methoxybenzyl bromide for the benzyl bromide (as utilized in Example VII), the corresponding, 1,2-diamino-4-(substituted-benzylthio)-benzene and 5(6)-(substituted-benzylthio)-2-carbomethoxyaminobenzimidazole compounds are prepared. By reacting the 1,2-diamino-(4-substituted-benzylthio)benzene compounds so prepared with 1,3-bis-ethoxycarbonyl-S-methyl isothiourea, 1,3-bis-propoxycarbonyl-S-methyl isothiourea, or 1,3-bis-butoxycarbonyl-S-methyl isothiourea instead of 1,3-bis-methoxycarbonyl-S-methyl isothiourea, the corresponding 5(6)-(substituted-benzylthio)-2-carbalkoxyaminobenzimidazole compounds are prepared, where R is either ethyl, propyl or butyl.

EXAMPLE VII 2.37 G. 1-acetamido-2-nitro-4-thiocyanatobenzene in 10 ml. dimethylformamide under nitrogen is treated with 0.38 g. sodium borohydride at 20°–25° C. After 1 hour 2.4 ml. benzylbromide is added, the mixture left for 2 hours, then diluted with water, filtered, washed with cyclohexane, recrystallized from methanol yielding 1-acetamido2-nitro-4-benzylthiobenzene.

2.42 G. 1-acetamido-2-nitro-4-benzylthiobenzene in 25 ml. chloroform is treated at −20 to −15° C with 1.6 g. 40% peracetic acid in 2 ml. methanol. The mixture is allowed to warm slowly to room temperature, held for 6 hours and washed with sodium bisulfite solution and sodium bicarbonate solution, dried and stripped. The residue is recrystallized from methanol giving 1-acetamido-2-nitro-4-benzylsulfinylbenzene. 2.14 G. 1-acetamido-2-nitro-4-benzylsulfinylbenzene is treated with 4 ml. 5N sodium hydroxide and 12 ml. methanol, on steam bath for 30 minutes, diluted with water, and filtered to give 1-amino-2-nitro-4-benzylsulfinylbenzene.

1.8 G. 1-amino-2-nitro-4-benzylsulfinylbenzene is treated in 120 ml. methanol and 30 ml. water with 1.8 g. iron powder and 0.9 g. ferrous sulfate at reflux for four hours, filtered and the filtrate concentrated under vacuum. The residue is extracted into chloroform and isolated by evaporation. The residue is recrystallized from methylene chloride-benzene giving 1,2-diamino-4-benzylsulfinylbenzene.

0.55 G. 1,2-diamino-4-benzylsulfinylbenzene and 0.44 g. 1,3-bis-methoxycarbonyl-S-methyl isothiourea and 0.15 ml. acetic acid in 20 ml. ethanol and 20 ml. water is refluxed for four hours, filtered, and the crude product recrystallized from ethanol and giving 5(6)-benzylsulfinyl-2-carbomethoxyaminobenzimidazole (m.pt. 224.5°–6°).

In a similar manner substituting p-chlorobenzyl bromide, p-methylbenzyl bromide and p-methoxybenzyl bromide for the benzyl bromide, the corresponding 1,2-diamino-4-(substituted-benzylsulfinyl)benzene and 5(6)-(substituted benzylsulfinyl)-2-carbomethoxyaminobenzimidazole compounds are prepared. By reacting the 1,2-diamino-4-(substituted-benzylsulfinyl)benzene compounds so prepared with 1,3-bis-ethoxycarbonyl-S-methyl isothiourea, 1-3-bis-propoxycarbonyl-S-methyl isothiourea, or 1,3-bis-butoxycarbonyl-S-methyl isothiourea instead of 1,3-bis-methoxycarbonyl-S-methyl isothiourea, the corresponding 5(6)-(substituted-benzylsulfinyl)-2-carbalkoxyaminobenzimidazole compounds are prepared, where R is either ethyl, propyl or butyl.

EXAMPLE VIII

1-Acetamido-2-nitro-4-benzylthiobenzene or the 1-acetamido-2-nitro-4-(substituted-benzylthiobenzenes) of Example VI are treated with an excess of peracetic acid under the conditions as set forth in the second paragraph of Example VII, but for a longer period of time, to afford 5(6)-benzylsulfonyl-2-carbalkoxyaminobenzimidazole or the corresponding 5(6)-(substituted-benzylsulfonyl)-2-carbalkoxyaminobenzimidazoles. These compounds can also be prepared in similar manner from 5(6)-benzylsulfinyl-2-carbalkoxyaminobenzimidazole or the corresponding 5(6)-(substituted-benzylsulfinyl)-2-carbalkoxyaminobenzimidazole prepared according to Example VII.

EXAMPLE IX

5 G. of 2-amino-4-chloro-1-nitrobenzene is added to a solution of sodium phenyl mercaptide, prepared under nitrogen from 2.53 g. 57% sodium hydride and 6.2 ml. thiophenol in 20 ml. dimethylformamide, with a 10 ml. dimethylformamide rinse. The mixture is stirred under nitrogen for three hours at 20°–30° C and then diluted with water. The crude product is washed with water and hexane, then recrystallized from methanol, yielding 2-amino-4-phenylthio-1-nitrobenzene. 6.0 G. of 2-amino-4-phenylthio-1-nitrobenzene is dissolved in 80 ml. acetic anhydride and treated with a few drops of sulfuric acid. The mixture is left at 20°–30° C for 2 hours then a little sodium acetate added and the solvent removed under vacuum. The residue is treated with water, filtered and recrystallized from methanol yielding 2-acetamido-4-phenylthio-1-nitrobenzene. This material may also be obtained by reaction of 2-acetamido-4-chloro1-nitrobenzene with sodium phenylmercaptide essentially as described above for the free amine.

7.0 G. of 2-acetamido-4-phenylthio-1-nitrobenzene is dissolved in 70 ml. chloroform and treated, at −20° to −15° C, with a solution of 5.0 g. 40% peracetic acid in 10 ml. methanol. The mixture is allowed to warm slowly to 20° C and stirred for four hours. The reaction mixture is extracted with sodium bisulfite solution, then sodium bicarbonate solution, dried and evaporated. The residual gum of 2-acetamido-4-phenylsulfinyl-1-nitrobenzene is treated with 20 ml. 5N sodium hydroxide and 40 ml. methanol at 20°–25° C for 1 hour. Water is then added and essentially pure 2-amino-4-phenylsulfinyl-1-nitrobenzene filtered off. Recrystallization may be effected from benzene.

5.4 G. of 2-amino-4-phenylsulfinyl-1-nitrobenzene is hydrogenated at 1 atmosphere pressure in 500 ml. methanol in the presence of 5 g. 5% palladized carbon, until the theoretical uptake of hydrogen has occurred. The catalyst is removed by filtration and the filtrate stripped under vacuum. The residue is recrystallized from methanol-benzene, yielding 1,2-diamino-4-phenylsulfinylbenzene.

A mixture of 5.5 g. of 1,2-diamino-4-phenylsulfinylbenzene, 4.3 g. of 1,3-bis-methoxycarbonyl-S-methyl isothiourea and 1.2 ml. acetic acid in 100 ml. ethhanol and 100 ml. water is refluxed for four hours. The mixture is cooled and essentially pure 5(6)-phenylsulfinyl-2-carbomethoxyaminobenzimidazole filtered off and washed with methanol. Recrystallization may be effected from methanolchloroform (m.pt. 253° dec.).

In a similar manner, substituting 1,3-bis-ethoxycarbonyl-S-methyl isothiourea, 1,3-bis-propoxycarbonyl-S-methyl isothiourea, or 1,3-bis-butoxycarbonyl-S-methyl isothiourea, for the 1,3-bis-methoxycarbonyl-S-methyl isothiourea, the corresponding 2-carbalkoxyamino-5(6)-phenylsulfinylbenzimidazole compounds are prepared, where R is ethyl, propyl or butyl.

In a similar manner, substituting sodium naphth-2-ylmercaptide for the sodium phenyl mercaptide, 5(6)-(naphth-2-ylsulfinyl)-2-carbomethoxyaminobenzimidazole is prepared.

EXAMPLE X

A mixture of 2.5 g. 2-amino-4-chloro-1-nitrobenzene, 3.6 g. p-thiocresol, 4.2 g. potassium carbonate in 20 ml. dimethylformamide is stirred overnight at room temperature, then poured into water. The crude product, recrystallized from methanol, gives 2-amino-4-(p-methylphenylthio)-1-nitrobenzene.

3.35 G. of 2-amino-4-(p-methylphenylthio)-1-nitrobenzene in 16 ml. concentrated hydrochloric acid and 16 ml. acetic acid is treated with 16 g. stannous chloride on the steam bath for 1 hour. The mixture is cooled, treated with an excess of potassium bicarbonate and extracted with chloroform. Evaporation of the chloroform leaves 1,2-diamino-4-(p-methylphenylthio) benzene.

2.5 G. 1,2-diamino-4-(p-methylphenylthio)benzene and 2.35 g. 1,3-bis-methoxycarbonyl-S-methyl isothiourea and 0.75 ml. acetic acid in 50 ml. water and 50 ml. ethanol are refluxed 3 hours. The mixture is filtered and the product recrystallized from methanol-chloroform, yielding 2-(carbomethoxyamino)-5(6)-(p-methylphenylthio)-benzimidazole.

1.88 G. 5(6)-p-methylphenylthio-2-carbomethoxyaminobenzimidazole is dissolved in a mixture of 150 ml. acetic acid and 150 ml. chloroform. A solution of 1.22 g. metachloroperbenzoic acid in 20 ml. chloroform is added at −15° to −10° C, then the mixture is allowed to warm slowly to 20 to 25° C. After 6 hours, the solvent is removed under vacuum at 20°–30° C and the residue treated with sodium bicarbonate solution. The product is filtered off and recrystallization from methanol-chloroform gives 5(6)-p-methylphenylsulfinyl-2-carbomethoxyaminobenzimidazole (m.pt. 265°–7°).

In a similar manner using p-chlorophenyl mercaptide, p-methoxyphenyl mercaptide, and p-fluorophenyl mercaptide, in place of the p-thiocresol, 5(6)-p-chlorophenylsulfinyl2-carbomethoxyaminobenzimidazole, 5(6)-p-methoxyphenylsulfinyl-2-carbomethoxyaminobenzimidazole, and 5(6)-p-fluorophenylsulfinyl-2-carbomethoxyaminobenzimidazole, respectively, are prepared.

Also in a similar manner, using any of the 1,2-diamino compounds prepared above in this Example and substituting 1,3-bis-ethoxycarbonyl-S-methyl isothiourea, 1,3-bis-propoxycarbonyl-S-methyl isothiourea, or 1,3-bis-butoxycarbonyl-S-methyl isothiourea for 1,3-bis-methoxycarbonyl-S-methyl isothiourea, the corresponding 5(6)-p-methylphenylsulfinyl-, 5(6)-p-chlorophenylsulfinyl-, 5(6)-p-methoxyphenylsulfinyl- and 5(6)-p-fluorophenylsulfinyl-2-carbalkoxyaminobenzimidazole compounds are prepared, where R is ethyl, propyl or butyl.

EXAMPLE XI 2.0 g. of 2 amino-4-chloro-1-nitrobenzene and 5.0 g. sodium benzene-sulfinate in 20 ml. dimethylformamide is heated at reflux for 3 hours. The mixture is cooled, diluted with water and the product filtered off to give 2-amino-1-nitro-4-phenylsulfonylbenzene.

1.9 g. of 2-amino-1-nitro-4-phenylsulfonylbenzene is treated in methanol with hydrogen at 4 atmospheres in the presence of Raney nickel catalyst for 2 hours. The catalyst if filtered off and the filtrate stripped under vacuum. Recrystallization of the residue gives 1,2-diamino-4-phenylsulfonylbenzene.

0.75 g. of 1,2-diamino-4-phenylsulfonylbenzene and 0.68 g. 1,3-bismethoxycarbonyl-S-methyl isothiourea and 0.2 ml. acetic acid in 10 ml. ethanol and 10 ml. water, is refluxed for 4 hours. The product is filtered off. Recrystallization from methanol-chloroform yields 5(6)-phenylsulfonyl-2-carbomethoxyaminobenzimidazole.

In a similar manner substituting 1,3-bis-ethoxycarbonyl-S-methyl isothiourea, 1,3-bis-propoxycarbonyl-S-methyl isothiourea, or 1,3-bis-butoxycarbonyl-S-methyl isothiourea for the 1,3-bis-methoxycarbonyl-S-methyl isothiourea, the corresponding 5(6)-phenylsulfonyl-2-carbalkoxyaminobenzimidazole compounds are prepared, where R is either ethyl, propyl or butyl.

EXAMPLE XII

The 5(6)-(p-substituted phenylthio)-2-carbalkoxyaminobenzimidazoles of Example X are treated with an excess of m-chloroperbenzoic acid under conditions as set forth in Example X, but for a longer period of time, to afford the corresponding 5(6)-(p-substituted phenylsulfonyl)-2-carbalkoxyaminobenzimidazoles. These compounds can also be prepared in similar manner from the 5(6)-(p-substituted phenylsulfinyl)-2-carbalkoxyaminobenzimidazoles prepared according to Example X.

EXAMPLE XIII 2.94 G. of 1-acetamido-4-hydroxy-2-nitrobenzene, 5.13 g. of benzyl bromide and 4.2 g. anhydrous potassium carbonate are refluxed overnight in acetone with stirring, evaporated to dryness, the excess benzyl bromide removed under vacuum, water added and the product extracted with dichloromethane to give 1-acetamido-4-benzyloxy-2-nitrobenzene.

The 1-acetamido-4-benzyloxy-2-nitrobenzene so produced is treated with sodium hydroxide in methanol, warmed briefly on a steam bath for about 15 minutes until the reaction is complete, diluted with water and extracted with dichloromethane to give 1-amino-4-benzyloxy-2-nitrobenzene.

2.44 G. of 1-amino-4-benzyloxy-2-nitrobenzene is stirred in 100 ml. methanol and 100 ml. 20% hydrochloric acid with 1.0 g. iron powder at room temperature. After 2 hours, the mixture is poured into excess ammonium hydroxide solution, the residue extracted with chloroform, filtered under nitrogen, dried over magnesium sulfate, filtered once again, and evaporated to dryness to give 1,2-diamino-4-benzyloxybenzene.

5 G. of 1,2-diamino-4-benzyloxybenzene, 5 g. 1,3-bis-methoxycarbonyl-S-methyl thiourea and 1.8 g. acetic acid are dissolved in 50 ml. ethanol plus 50 ml. water and the solution is refluxed for 3 hours. The mixture is cooled and 5(6)-benzyloxy-2-carbomethoxyaminobenzimidazole is filtered off and washed with methanol.

In a similar manner substituting p-chlorobenzyl bromide, p-methylbenzyl bromide and p-methoxybenzyl bromide for the benzyl bromide, the corresponding 1,2-diamino-4-substituted benzyloxy benzene and 2-carbomethoxyamino-5(6)-substituted benzyloxy-benzimidazole compounds are prepared. By reacting the 1,2-diamino-4-substituted benzyloxy benzene compounds so prepared with 1,3-bis-ethoxycarbonyl-S-methyl isothiourea, 1,3-bis-propoxycarbonyl-S-methyl isothiourea, or 1,3-bis-butoxycarbonyl-S-methyl isothiourea instead of 1,3-bis-methoxycarbonyl-S-methyl isothiourea, the corresponding 2-carbalkoxyamino-5(6)-substituted benzyloxy-benzimidazole compounds are prepared, where R is either ethyl, propyl or butyl.

EXAMPLE XIV 1-acetamido-4-hydroxy-2-nitrobenzene is treated with the alkenyl or alkynyl halides of Example III under the conditions (or similar or analogous conditions) as set forth in Example XIII to afford the corresponding 5(6)-alkenyloxy-2-carbalkoxybenzimidazoles or the corresponding 5(6)-alkynyloxy-2-carbalkoxybenzimidazoles.

EXAMPLE XV 2.37 G. of 1-acetamido-2-nitro-4-thiocyanatobenzene in 10 ml. dimethylformamide is treated at 20°–25° C under nitrogen, with 0.38 g. of sodium borohydride. After 1 hour 1.6 ml. of chloromethyl methyl ether is added, and the mixture kept at 20°–30° C for a further three hours. Water is then added and the product filtered off. Recrystallization from cyclohexane gives 1-acetamido-2-nitro-4-methoxymethylthiobenzene.

1.4 G. of 1-acetamido-2-nitro-4-methoxymethylthiobenzene is treated with 3 ml. 5N sodium hydroxide and 6 ml. methanol in the steam bath for about 15 minutes. The mixture is stripped under vacuum and the residue extracted with chloroform. The dried extracts are evaporated giving 1-amino-2-nitro-4-methoxymethylthiobenzene as a red crystalline solid.

1.3 G. of 1-amino-2-nitro-4-methoxymethylthiobenzene is treated in 80 ml. methanol and 20 ml. water at reflux under nitrogen, with 0.7 g. ferrous sulfate and 2.8 g. iron (added in two portions) for four hours. The mixture is filtered, stripped under vacuum, and the residue recrystallized from cyclohexane. 1,2-Diamino-4-methoxymethylthiobenzene is thus obtained.

0.85 G. of 1,2-diamino-4-methoxymethylthiobenzene and 1.0 g. 1,3-bis-methoxycarbonyl-S-methyl isothiourea in 25 ml. ethanol and 25 ml. water is treated at reflux with 0.7 ml. acetic acid. After 4 hours the mixture is cooled and filtered, yielding 5(6)-methoxymethylthio-2-carbomethoxyamino-benzimidazole, which may be recrystallized from methanol-chloroform (m.pt. 200°–201.5° C).

In a similar manner substituting chloroethyl methyl ether, chloropropyl methyl ether, chlorobutyl methyl ether, chloromethyl ethyl ether, chloromethyl propyl ether, or chloromethyl butyl ether, in place of the chloromethyl methyl ether, the corresponding 1,2-diamino-4-alkoxyalkylthiobenzene and 5(6)-alkoxyalkylthio-2-carbomethoxyaminobenzimidazole compounds are prepared. Also in a similar manner substituting 1,3-bis-ethoxycarbonyl-S-methyl isothiourea, 1,3-bis-propoxycarbonyl-S-methyl isothiourea, or 1,3-bis-butoxycarbonyl-S-methyl isothiourea for the 1,3-bis-methoxycarbonyl-S-methyl isothiourea, the corresponding 5(6)-alkoxyalkylthio-2-carbalkoxyaminobenzimidazole compounds are prepared where R is either ethyl, propyl or butyl.

EXAMPLE XVI 5.85 G. 1-amino-2-nitro-4-thiocyanatobenzene is treated in 20 ml. dimethylformamide under nitrogen at 20°–25° C. with 1.14 g. sodium borohydride. After 1 hour 10 ml. of methylthiomethylchloride is added and the mixture stirred overnight, diluted with water and extracted with chloroform. The dried chloroform solution is passed through a silica gel column, then evaporated to dryness leaving 1-amino-2-nitro-4-methylthiomethylthiobenzene as a red solid.

2.5 G. of 1-amino-2-nitro-4-methylthiomethylthiobenzene in 160 ml. methanol and 40 ml. water is treated at reflux for 5 hours with 1.25 g. ferrous sulfate and 5 g. iron powder (the latter added in 2 portions). The mixture is filtered, stripped and the residual oily 1,2-diamino-4-methylthiomethylthiobenzene extracted into chloroform, washed, dried and isolated by evaporation of the solvent.

1.8 G. 1,2-diamino-4-methylthiomethylthiobenzene and 1.9 g. 1,3-bis-methoxycarbonyl-S-methyl isothiourea and 0.8 ml. acetic acid in 20 ml. ethanol plus 20 ml. water are refluxed for 5 hours, cooled and filtered. The product, 5(6)-methylthiomethylthio-2-carbomethoxyaminobenzimidazole, is purified by recrystallization from methanol-chloroform (m.pt. 208°–210.5° C).

In a similar manner using ethylthiomethyl chloride, propylthiomethyl chloride, butylthiomethyl chloride, methylthioethyl chloride, methylthiopropyl chloride, methylthiobutyl chloride, ethylthioethyl chloride or ethylthiopropyl chloride in place of the methylthiomethyl chloride, the corresponding 1,2-diamino-4-alkylthioalkylthiobenzene and 5(6)-alkylthioalkylthio-2-carbomethoxyaminobenzimidazole compounds are prepared. By reacting the 1,2-diamino-4-alkylthioalkylthiobenzenes so prepared with 1,3-bis-ethoxycarbonyl-S-methyl isothiourea, 1,2-bis-propoxycarbonyl-S-methyl isothiourea, or 1,3-bis-butoxycarbonyl-S-methylisothiourea instead of 1,3-bis-methoxycarbonyl-S-methyl isothiourea, the corresponding 5(6)-alkylthioalkylthio-2-carbalkoxyaminobenzimidazole compounds are prepared, where R is either ethyl, propyl or butyl.

EXAMPLE XVII

6 G. of 1-acetamido-4-hydroxy-2-nitrobenzene is added to 200 ml. acetone containing 25 g. potassium carbonate and 6 ml. chloromethyl methyl sulfide. The mixture is heated at reflux for four hours and is filtered. The acetone is evaporated leaving 1-acetamido-4-methylthiomethoxy-2-nitrobenzene as a gum. This is purified by column chromatography.

5.7 G. of 1-acetamido-4-methylthiomethoxy-2-nitrobenzene is added to a mixture of 12 ml. 5N NaOH and 60 ml. methanol and the mixture heated for 15 minutes on a steam bath. The mixture is poured into 500 ml. water and is extracted with methylene chloride. The methylene chloride layer is separated, dried over sodium sulfate, and evaporated leaving 1-amino-4-methylthiomethoxy-2-nitrobenzene as a gum. This gum is dissolved in a mixture of 5 ml. acetic acid and 95 ml. methanol. 8 G. of iron powder is added and the mixture is heated at reflux for 2 hours. The methanol and acetic acid are evaporated and the residue is extracted with 200 ml. hot tetrahydrofuran. This solution is filtered and the tetrahydrofuran evaporated to yield 1,2-diamino-4-methylthiomethoxybenzene as a gum. This is purified by column chromatography.

4.1 G. of 1,2-diamino-4-methylthiomethoxybenzene, 5 g. 1,3-bis-methoxycarbonyl-S-methyl isothiourea and 1 g. acetic acid are dissolved in 50 ml. ethanol plus 50 ml. water and the solution is refluxed for three hours. The mixture is cooled and 5(6)-methylthiomethoxy-2-carbomethoxyaminobenzimidazole is filtered off and washed with methanol. Recrystallization may be effected from methanol-chloroform.

In a similar manner substituting chloroethyl methyl sulfide, chloropropyl methyl sulfide, chlorobutyl methyl sulfide, chloromethyl ethyl sulfide, chloromethyl propyl sulfide, or chloromethyl butyl sulfide for the chloromethyl methyl sulfide, the corresponding 1,2-diamino-4-alkylthioalkoxybenzene and 5(6)-alkylthioalkoxy-2-carbomethoxyaminobenzimidazole compounds are prepared. By reacting the 1,2-diamino-4-alkylthioalkoxybenzene compounds so prepared with 1,3-bis-ethoxycarbonyl-S-methyl isothiourea, 1,3-bis-propoxycarbonyl-S-methyl isothiourea, or 1,3-bis-butoxycarbonyl-S-methyl isothiourea instead of 1,3-bis-methoxycarbonyl-S-methyl isothiourea, the corresponding 5(6)-alkylthioalkoxy-2-carbalkoxyaminobenzimidazole compounds are prepared, where R is either ethyl, propyl or butyl.

EXAMPLE XVIII 1-acetamido-4-hydroxy-2-nitrobenzene is treated with chloromethyl methyl ether, chloroethyl methyl ether, chloropropyl methyl ether, chlorobutyl methyl ether, chloromethyl ethyl ether, chloromethyl propyl ether, chloromethyl butyl ether, chloroethyl ethyl ether, and chloroethyl propyl ether, respectively, under the conditions (or similar or analogous conditions) as set forth in Example XVII to afford the corresponding 5(6)-alkoxyalkoxy-2-carbalkoxyaminobenzimidazoles, including 5(6)-methoxymethoxy-2-carbalkoxyaminobenzimidazole.

EXAMPLE XIX 2.4 Grams of 100% sodium hydride is dissolved in 120 ml. of 2-methoxyethanol and 12 g. of 2-nitro-5-chloroaniline is added. The mixture is refluxed for 4 hours, cooled and poured into water. 2-Nitro-5-(2-methoxyethoxy) aniline is collected by filtration.

A mixture of 11 g. of 2-nitro-5-(2-methoxyethoxy) aniline, 220 ml. of methanol, 460 ml. of water, 40 g. sodium carbonate and 60 g. sodium hydrosulfite is refluxed for 15 minutes. The solution is concentrated, diluted with water and extracted with chloroform. Evaporation of the chloroform leaves 1,2-diamino-4-(2-methoxyethoxy) benzene as an oil, sufficiently pure for the next step.

A mixture of 1.8 g. of 1,2-diamino-4-(2-methoxyethoxy) benzene, 2.2 g. of 1,3-bis(methoxycarbonyl)-S-methyl-isothiourea, 0.8 ml. of acetic acid in 20 ml. of ethanol and 20 ml. of water is refluxed for 4 hours. The cooled mixture is filtered, yielding 5(6)-(2-methoxyethoxy)-2-carbomethoxyaminobenzimidazole which may be recrystallized from methanolchloroform.

EXAMPLE XX

A mixture of 5 g. of 2-nitro-5-chloroaniline and 7.5 g. of sodium sulfide monohydrate in 25 ml. of ethanol and 25 ml. water is refluxed for 1 hour, diluted with water to about 150 ml. total volume and filtered to remove a small amount of insoluble impurity. The filtrate is treated with 2.5 ml. of acetic acid and 2-nitro-5-mercaptoaniline filtered off.

A solution of 3.4 g of 2-nitro-5-mercaptoaniline in 20 ml. of DMF is treated with 0.5 g. of 100% sodium hydride, and 2.2 g. of chloromethyl-ethyl ether is added to the solution. After 30 minutes at 20–25° C, the solution is diluted with water and extracted with chloroform. Removal of the chloroform leaves 2-nitro-5-(ethoxymethylthio) aniline as an oil.

The above oil is treated for 15 minutes in a boiling mixture of 50 ml. of methanol, 50 ml. of water, 12 g. of sodium carbonate and 12 g. of sodium hydrosulfite. The mixture is concentrated, diluted with water and extracted thoroughly with chloroform. Evaporation of the chloroform leaves 1,2-diamino-4-ethoxymethylthiobenzene as an oil.

A mixture of 2.6 g. of the above oil, 2.6 g. of 1,3-bis(-methoxycarbonyl)-S-methyl-isothiourea and 1 ml. of acetic acid is treated with 40 ml. of refluxing 50% aqueous ethanol for 4 hours. The cooled mixture is filtered yielding 5(6)-ethoxymethylthio-2-carbomethoxyaminobenzimidazole, which may be recrystallized from methanol-chloroform.

0.84 G. of 5(6)-ethoxymethylthio-2-carbomethoxyaminobenzimidazole is dissolved in a mixture of 50 ml. of chloroform and 10 ml of acetic acid. The solution is treated at −30° to −20° C with a solution of 0.62 g. of m-chloroperbenzoic acid in 15 ml. of chloroform, then allowed to warm slowly to room temperature. After 15 hours the solvent is removed under vacuum and the residue treated with dilute potassium bicarbonate solution. The crude 5(6)-ethoxymethylsulfinyl-2-carbomethoxyaminobenzimidazole is filtered off and recrystallized from methanol-chloroform.

EXAMPLE XXI

A solution of 2.37 g. of 1-acetamido-2-nitro-4-thiocyanatobenzene in 10 ml. of DMF is treated under nitrogen at 20–30° C, with 0.38 g. of sodium borohydride. After 1 hour, 1.6 ml. of chloromethylmethylether is added at 20–30° C, then after a further 3 hours, the mixture is diluted with water and filtered. The crude 1-acetamido-2-nitro-4-methoxymethylthiobenzene is recrystallized from cyclohexane.

1.4 G. of 1-acetamido-2-nitro-4-methoxymethylthiobenzene is treated in 6 ml. of methanol with 3 ml. of 5N aqueous sodium hydroxide solution and refluxed for 15 minutes. The solvent is removed under vacuum and the residue diluted with water and extracted with chloroform. Evaporation of the chloroform yields 2-nitro-4-methoxymethylthioaniline as reddish crystals.

1.4 G. of the above aniline compound is treated, in a refluxing mixture of 80 ml. of methanol and 20 ml. of water, with 1.4 g. of iron powder and 0.7 g. of ferrous sulfate. After 2 hours, an additional 1.4 g. of iron is added. After about 1 to 2 hours more, the mixture is filtered and the filtrate concentrated under vacuum. The residual 1,2-diamino-4-methoxymethylthiobenzene is recrystallized from cyclohexane.

1.7 G. of 1,2-diamino-4-methoxymethylthiobenzene is treated, in 50 ml. of refluxing 50% aqueous ethanol, with 2.0 g. of 1,3-bis(methoxycarbonyl)-S-methyl isothiourea and 0.7 ml. of acetic acid for 4 hours. The mixture is cooled and the 5(6)-methoxymethylthio-2-carbomethoxyaminobenzimidazole filtered off. Recrystallization may be effected from methanol-chloroform.

0.53 G. of the above benzimidazole is dissolved in a mixture of 50 ml. of chloroform and 50 ml. of acetic acid at −15° C. A solution of 0.41 g. m-chloroperbenzoic acid in 10 ml. of chloroform is added at −15° to −10° C, and the mixture is then allowed to warm to 20° −25° C. After 10 hours at 20° −25° C, the solvent is removed under vacuum and the residue treated carefully with dilute sodium bicarbonate solution (to pH of about 7). The crude product is filtered off and recrystallized from methanol-chloroform, yielding 5(6)-methoxymethylsulfinyl-2-carbomethoxyaminobenzimidazole.

EXAMPLE XXII

A mixture of 4 g. of 4-hydroxy-6-nitroacetanilide, 17 g. of potassium carbonate and 4 g. of chloromethyl methylether in 50 ml. of acetone under nitrogen is refluxed for 4 hours. The hot mixture is diluted with 200 ml. of hot acetone and is then filtered. The solvent is evaporated and 2-nitro-4-methoxymethoxyacetanilide is obtained as a red oil.

4.5 G. of 2-nitro-4-methoxymethoxyacetanilide is heated for one-half hour with 10 ml. of 5N sodium hydroxide solution and 60 ml. of methanol. The solution is then cooled, diluted with water and the 2-nitro-4-methoxymethoxyaniline filtered off.

A mixture of 3.5 g. of 2-nitro-4-methoxymethoxyaniline, 1 g. of 5% palladium-on-charcoal catalyst and 120 ml. of methanol is hydrogenated at ambient conditions. After the uptake of hydrogen is complete, the mixture is filtered and 1,2-diamino-4-methoxymethoxybenzene is obtained by evaporation of the solvent.

3.0 G. of 1,2-diamino-4-methoxymethoxybenzene in 15 ml. of ethanol, 15 ml. of water, and 0.5 ml. of acetic acid is treated with 3.0 g. 1,3-bis(methoxycarbonyl)-S-methyl isothiourea, at reflux, for 4 hours. The mixture is cooled, filtered, and the product recrystallized from methanolchloroform yielding 5(6)-methoxymethoxy-2-carbomethoxyaminobenzimidazole.

EXAMPLE XXIII

A mixture of 6 g. of 4-hydroxy-6-nitroacetanilide, 25 g. of potassium carbonate, 5 g. of chlorodimethylsulfide in 200 ml. of acetone is refluxed for 4 hours under nitrogen. The hot mixture is diluted with 300 ml. of hot acetone and is filtered. The solvent is evaporated and the oil obtained is chromatographed on silica gel with chloroform as the eluant. Pure 2-nitro-4-methylthiomethoxyacetanilide is obtained from the eluate.

5.7 G. of 2-nitro-4-methylthiomethoxyacetanilide is treated with 12 ml. of 5N sodium hydroxide solution and 60 ml. of methanol, and the solution is heated for one-half hour. The solution is cooled, diluted with water, and extracted with chloroform. The chloroform solution is dried over sodium sulfate and is evaporated to give 2-nitro-4-methylthiomethoxyaniline.

4.5 g. of 2-nitro-4-methylthiomethoxyaniline in 95 ml. of methanol and 5 ml. of acetic acid is treated with 8 g. of iron powder and the mixture is refluxed for 4 hours. The hot solution is filtered and the solvent evaporated. The residue is treated with hot tetrahydrofuran. The mixture is filtered and the solvent evaporated to give 1,2-diamino-4-methylthiomethoxybenzene.

3.9 G. of 1,2-diamino-4-methylthiomethoxybenzene in 25 ml. of ethanol, 25 ml. of water, and 0.6 ml. of acetic acid is treated with 5.0 g. of 1,3-bis(methoxycarbonyl)-Smethyl isothiourea, at reflux, for 4 hours. The mixture is cooled, filtered, and the product recrystallized from tetrahydrofuran yielding 5(6)-methylthiomethoxy-2-carbomethoxyaminobenzimidazole.

EXAMPLE XXIV

A mixture of 2.5 g. of 4-hydroxy-6-nitroacetanilide, 2.1 g. of 2-bromoethyl ethylether, and 3.6 g. of potassium carbonate in 25 ml. of dimethylformamide is heated to 110° C under nitrogen for 16 hours. The mixture is cooled, diluted with water, and 4-(2-ethoxyethoxy)-2-nitroacetanilide is isolated by filtration.

2.3 G. of 4-(2-ethoxyethoxy)-2-nitroacetanilide is heated for one-half hour with 5 ml. of 5N sodium hydroxide solution and 30 ml. of methanol. The mixture is cooled, diluted with water, and 4-(2-ethoxyethoxy)-2-nitroaniline isolated by filtration.

A mixture of 1.8 g. of 4-(2-ethoxyethoxy)-2-nitroaniline and 0.3 g. of 5% palladium-on-charcoal catalyst in 200 ml. of methanol is hydrogenated under ambient conditions. After the uptake of hydrogen is complete, the mixture is filtered and 1,2-diamino-4-(2-ethoxyethoxy) benzene is isolated from the filtrate by evaporation.

1.6 G. of 1,2-diamino-4-(2-ethoxyethoxy) benzene in 12 ml. of ethanol, 12 ml. of water and 0.3 ml. of acetic acid is treated with 2 g. of 1,3-bis(methoxycarbonyl)-S-methyl isothiourea, at reflux, for 4 hours. The mixture is cooled, filtered, and the product recrystallized from methanol-chloroform yielding 5(6)-(2-ethoxyethoxy)-2-carbomethoxyaminobenzimidazole.

In a similar manner using 2-bromoethylphenylether, 5(6)-(2-phenoxyethoxy)-2-carbomethoxyaminobenzimidazole is prepared.

EXAMPLE XXV

6 G. of 1-amino-2-nitro-4-thiocyanatobenzene in 20 ml. of dimethylformamide is treated under nitrogen with 1.17 g. of sodium borohydride in 10 ml. of dimethylformamide at not greater than 30° C. The mixture is stirred at 15° to 20° C for one hour, then treated with 5 g. of 2-bromoethyl ethylether at 20° -25° C. The mixture is heated to 100° C for 2 hours, then cooled and diluted with water. The product is extracted with chloroform and after drying of the chloroform solution with sodium sulfate, 1-amino-2-nitro-4-(2-ethoxyethylthis) benzene is obtained by evaporation of the solution.

6.4 G. of 1-amino-2-nitro-4-(2-ethoxyethylthio) benzene in 100 ml. of methanol and 50 ml. of water is treated with 16 ml. of sodium dithionite and 14 g. sodium carbonate at reflux under nitrogen. Heating is continued for one-half hour, then the methanol is evaporated from the mixture. The mixtue is diluted with 100 ml. of water and is extracted with chloroform. The chloroform solution is dried over sodium sulfate and 1,2-diamino-4-(2-ethoxyethylthio) benzene is obtained by evaporation of the solution.

4.8 G. of 1,2-diamino-4-(2-ethoxyethylthio) benzene in 25 ml. of ethanol, 25 ml. of water and 1 ml. of acetic acid is treated with 7.5 g. of 1,3-bis(methoxycarbonyl)-S-methyl isothiourea, at reflux, for 4 hours. The mixture is cooled, filtered, and the product recrystallized from methanolchloroform to give 5(6)-(2-ethoxyethylthio)-2-carbomethoxyaminobenzimidazole.

In a similar fashion using 2-bromoethylmethylether, the corresponding 5(6)-(2-methoxyethylthio)-2-carbomethoxyaminobenzimidazole is prepared.

EXAMPLE XXVI 4.4 G. of 1-amino-2-nitro-4-thiocyanatobenzene in 10 ml. of dimethylformamide is treated under nitrogen with 0.85 g. of sodium borohydride in 10 ml. of DMF at not greater than 30° C. The mixture is stirred at 15° to 20° C for 1 hour, then treated with 5 g. of 1,1,1-trifluoro-2-bromoethane at 20° to 25° C. The mixture is heated to 100° C for 3 hours, cooled and diluted with water. The mixture is extracted with chloroform and the chloroform solution is dried over sodium sulfate. 2-Nitro-4-(2,2,2-trifluoroethylthio) aniline is obtained upon evaporation of the solution.

4.1 G. of 2-nitro-4-(2,2,2-trifluoroethylthio) aniline in 60 ml. of methanol and 12 ml. of water is treated with 1.25 g. of ferrous sulfate and 3.3. g. of iron powder at reflux. After 2 hours, 1.25 g. of ferrous sulfate and 3.3 g. of iron powder are added and heating is continued for 4 hours. The mixture is poured into 600 ml. of hot tetrahydrofuran and filtered. 1,2-Diamino-4-(2,2,2-trifluoroethylthio) benzene is obtained from the filtrate by evaporation.

3.4 G of 1,2-diamino-4-(2,2,2-trifluoroethylthio) benzene in 17 ml. of ethanol, 17 ml. of water and 1 ml. of acetic acid is treated with 3.5 g. of 1,3-bis(methoxycarbonyl)-S-methyl isothiourea, at reflux, for 4 hours. The mixture is cooled, filtered, and the product recrystallized from methanol-chloroform to give 5(6)-(2,2,2-trifluoroethylthio)-2-carbomethoxyaminobenzimidazole.

1.2 G. of 5(6)-(2,2,2-trifluoroethylthio)-2-carbomethoxyaminobenzimidazole in 480 ml. of chloroform, 120 ml. of methanol, and 2 ml. of acetic acid is treated with 0.75 g.of 85% m-chloroperbenzoic acid at 0° C. The solution is stirred for 1 hour, and then is extracted with saturated sodium bicarbonate solution and water. The chloroform solution is dried over sodium sulfate and evaporated. Recrystallization from methanol gives 5(6)-(2,2,2-trifluoroethylsulfinyl)-2-carbomethoxyaminobenzimidazole. In a similar manner using 5(6)-methylthiomethoxy-2-carbomethoxyaminobenzimidazole, of Example XXIII, 5(6)-methylsulfinylmethoxy-2-carbomethoxyaminobenzimidazole is prepared.

EXAMPLE XXVII 1.8 G. of 5(6)-2-(2-ethoxyethylthio)-2-carbomethoxyaminobenzimidazole of Example XXV in 200 ml. of chloroform and 1 ml. of acetic acid is treated with 1.55 g. of 30% peracetic acid in acetic acid solution at 15° C. The solution is stirred for 1 hour and then evaporated. The residue is triturated with diethylether and the solid is collected by filtration. Recrystallization from methanol-chloroform gives 5(6)-(2-ethoxyethylsulfinyl)-2-carbomethoxyaminobenzimidazole.

In a similar manner using 5(6)-(2-methoxyethylthio)-2-carbomethoxyaminobenzimidazole of Example XV, 5(6(2-methoxyethylsulfinyl)-2-carbomethoxyaminobenzimidazole is prepared.

EXAMPLE XXVIII

5 G. of 1-amino-2-nitro-4-thiocyanatobenzene in 20 ml. of dimethylformamide is heated under nitrogen with 0.97 g. of sodium borohydride in 20 ml. of dimethylformamide at not greater than 30° C. The mixture is stirred at 15° to 20° C for 1 hour, then treated with 6 g. of 1-iodo-2,2,3,3-tetrafluoropropane. The mixture is heated to 100° C for 4 hours, then cooled and diluted with water. The mixture is extracted with chloroform and the chloroform is evaporated to yield a red oil. Chromatography on silica gel gives 2-nitro-4-(2,2,3,3-tetrafluoropropylthio) aniline.

4 G. of 2-nitro-4-(2,2,3,3-tetrafluoropropylthio) aniline is treated with 24 g. of stannous chloride in 25 ml. on concentrated hydrochloric acid. The mixture is stirred for one-half hour, basified with ammonium hydroxide and extracted with chloroform. The chloroform solution is filtered, dried over sodium sulfate, and evaporated to give 1,2-diamino-4-(2,2,3,3-tetrafluoropropylthio) benzene.

3.5 G. of 1,2-diamino-4-(2,2,3,3-tetrafluoropropylthio) benzene in 20 ml. of ethanol, 20 ml. of water, and 0.8 ml. of acetic acid is treated with 4.5 g. of 1,3-bis(methoxycarbonyl)-S-methyl isothiourea, at reflux, for 4 hours. The mixture is cooled, filtered, and the produce recrystallized from methanol to give 5(6)-(2,2,3,3-tetrafluoropropylthio)2-carbomethoxyaminobenzimidazole.

10 G. of 5(6)-(2,2,3,3-tetrafluoropropylthio)-2-carbomethoxyaminobenzimidazole dissolved in 10 ml. of acetic acid is treated at 20° C with 0.8 g. of 30% peracetic acid in acetic acid solution. The solution is stirred for onehalf hour and diluted with 150 ml. of water. The mixture is filtered and the solid recrystallized from methanol to give 5(6)-(2,2,3,3-tetrafluoropropylsulfinyl)-2-carbomethoxyaminobenzimidazole.

EXAMPLE XXIX

In a similar manner to the procedure of Example XXVIII using (a) 1-iodo-2,2,3,3,3-pentafluoropropane, (b) the iron powder reduction step of Example XXIII (with 100 ml. of methanol, 10 ml. of acetic acid and 10 g. of iron powder), and (c) 4.1 g. of 1,2-diamino-4-(2,2,3,3,3-pentafluoropropylthio) benzene, 5 g. of 1,3-bis(methoxycarbonyl)-S-methyl isothiourea, 30 ml. of ethanol, 30 ml. of water and 1 ml. of acetic acid in the benzimidazole formation step, 5(6)-(2,2,3,3,3-pentafluoropropylthio)-2-carbomethoxyaminobenzimidazole and 5(6)-(2,2,3,3,3-pentafluoropropylsulfinyl)-2-carbomethoxyaminobenzimidazole are prepared.

EXAMPLE XXX

A mixture of 6.0 kg. of 1-amino-2-nitro-4-chlorobenzene and 7.2 kg. of potassium carbonate in 25 l. of DMF under nitrogen is treated with 4.0 kg. of thiophenol. The mixture is stirred for 2 hours, cooled, and diluted with 140 l. of ice water. The mixture is stirred for 1 hour, and 1-amino-2-nitro-5-phenylthiobenzene is isolated by filtration.

4.5 Kg. of 1-amino-2-nitro-5-phenylthiobenzene in 60 l. of methanol and 30 l. of water is treated, under nitrogen, with 8.0 kg. of sodium dithionite and 2.0 kg. of sodium carbonate at reflux. The mixture is heated for 2 hours and the methanol is removed by distillation. The mixture is cooled and extracted with dichloromethane. The dichloromethane solution is filtered, dried over sodium sulfate, and 1,2-diamino-4-phenylthiobenzene is isolated by evaporation.

3.25 Kg. of 1,2-diamino-4-phenylthiobenzene in 45 l. of ethanol, 45 l. of water, and 2 l. of acetic acid is treated with 4.3 kg. of 1,3-bis(methoxycarbonyl)-S-methyl isothiourea, at reflux, for 4 hours. The mixture is cooled and 5(6)-phenylthio-2-carbomethoxyaminobenzimidazole is isolated by filtration.

3.26 Kg. of 5(6)-phenylthio-2-carbomethoxyaminobenzimidazole in 30 l. of acetic acid is treated with 2.70 kg. of 30% peracetic acid in acetic acid solution. The solution is stirred for 1 hour and is diluted with 300 l. of water. 5(6)-Phenylsulfinyl-2-carbomethoxyaminobenzimidazole is isolated by filtration.

EXAMPLE XXXI

A drench powder is prepared having the following composition:

| | |
|---|---|
| 5(6)-phenylsulfinyl-2-carbomethoxyaminobenzimidazole | 30% |
| Carbowax 6000 | 40% |
| Myrj 52 [polyoxy] (40) stearate; a product of Atlas Chemical Co.] | 30% |

A liquid drench is prepared by mixing one ounce of this powder with one quart of water, and an appropriately-sized aliquot thereof (depending, inter alia, on the size of the animal and the frequency of administration) is administered to the animal being treated.

EXAMPLE XXXII

5 G. of 1-amino-2-nitro-4-thiocyanatobenzene in 15 ml. of DMF is treated under nitrogen with 0.97 g. of sodium borohydride in 10 ml. of DMF at not greater than 30° C. The mixture is stirred at 15° to 20° C. for 1 hour, then treated with 4.5 g. of 3-propionitrile at 20° to 25° C. The mixture is heated to 100° C. for 3 hours, cooled and diluted with water. The mixture is extracted with chloroform and the chloroform solution is dried over sodium sulfate. 1-Amino-2-nitro-4-(2-cyanoethylthio)benzene is obtained upon evaporation of the solution.

2.3 G. of 1-amino-2-nitro-4-(2-cyanoethylthio)benzene in 30 ml. of methanol and 6 ml. of water is treated with 2.5 g. of ferrous sulfate and 3.3 g. of iron powder at reflux. After 2 hours, 1.25 g. of ferrous sulfate and 3.3 g. of iron powder are added and heating is continued for four hours. The mixture is poured into 600 ml. of hot tetrahydrofuran and filtered. 1,2-Diamino-4-(2-cyanoethylthio)benzene is obtained from the filtrate by evaporation.

1.9 G. of the above diamino compound in 10 ml. of ethanol, 10 ml. of water and 1 ml. of acetic acid is treated with 2.1 g. of 1,3-bis(methoxycarbonyl)-S-methyl isothiourea at reflux for 4 hours. The mixture is cooled, filtered and the product recrystallized from methanol-chloroform to give 5(6)-(2-cyanoethylthio)-2-carbomethoxyaminobenzimidazole.

1.2 G. of 5(6)-(2-cyanoethylthio)-2-carbomethoxyaminobenzimidazole in 400 ml. of chloroform, 100 ml. of methanol and 2 ml. of acetic acid is treated with 0.85 g. of 85% m-chloroperbenzoic acid at 0° C. The solution is stirred for 1 hour, then is extracted with saturated sodium bicarbonate solution and water. The chloroform solution is dried over sodium sulfate and evaporated. Recrystallization from methanol gives 5(6)-(2-cyanoethylsulfinyl)-2-carbomethoxyaminobenzimidazole.

EXAMPLE XXXIII 4.4 G. of 1-amino-2-nitro-4-thiocyanatobenzene in 10 ml. of dimethylformamide is treated under nitrogen with 0.85 g. of sodium borohydride in 10 ml. of DMF at not greater than 30° C. The mixture is stirred at 15° to 20° C. for 1 hour, then treated with 5 g. of chloroacetonitrile at 20° to 25° C. The mixture is treated overnight at room temperature and poured into water. Filtration and recrystallization from methanol affords 1-amino-2-nitro-4-cyanomethylthiobenzene.

4.1 G. of 1-amino-2-nitro-4-cyanomethylthiobenzene in 60 ml. of methanol and 12 ml. of water is treated with 1.25 g. of ferrous sulfate and 3.3 g. of iron powder at reflux. After 2 hours, 1.25 g. of ferrous sulfate and 3.3 g. of iron powder are added and heating is continued for 4 hours. The mixture is poured into 600 ml. of hot tetrahydrofuran and filtered. 1,2-Diamino-4-cyanomethylthiobenzene is obtained from the filtrate by evaporation.

3.4 G. of 1,2-diamino-4-cyanomethylthiobenzene in 17 ml. of ethanol, 17 ml. of water and 1 ml. of acetic acid is treated with 3.5 g. of 1,3-bis(methoxycarbonyl)-S-methyl isothiourea, at reflux, for 4 hours. The mixture is cooled, filtered, and the product recrystallized from methanol-chloroform to give 5(6)-cyanomethylthio-2-carbomethoxyaminobenzimidazole.

1.2 G. of 5(6)-cyanomethylthio-2-carbomethoxyaminobenzimidazole in 480 ml. of chloroform, 120 ml. of methanol, and 2 ml. of acetic acid is treated with 0.75 g. of 85% m-chloroperbenzoic acid at 0° C. The solution is stirred for 1 hour, and then is extracted with saturated sodium bicarbonate solution and water. The chloroform solution is dried over sodium sulfate and evaporated. Recrystallization from methanol gives 5(6)-cyanomethylsulfinyl-2-carbomethoxyaminobenzimidazole.

EXAMPLE XXXIV

A mixture of 5 g. of 2-nitro-5-chloroaniline and 7.5 g. of sodium sulfide monohydrate in 25 ml. of ethanol and 25 ml. water is refluxed for 1 hour, diluted with water to about 150 ml. total volume and filtered to remove a small amount of insoluble impurity. The filtrate is treated with 2.5 ml. of acetic acid and 2-nitro-5-mercaptoaniline filtered off.

A solution of 3.4 g. of 2-nitro-5-mercaptoaniline in 20 ml. of DMF is treated with 0.5 g. of 100% sodium hydride, and 2.2 g. of chloromethylthiocyanate is added to the solution. After 30 minutes at 20°-25° C., the solution is diluted with water and extracted with chloroform. Removal of the chloroform leaves 1-amino-2-nitro-5-(thiocyanatomethylthio)benzene.

The above compound is treated for 15 minutes in a boiling mixture of 50 ml. of methanol, 50 ml. of water, 12 g. of sodium carbonate and 12 g. of sodium hydrosulfite. The mixture is concentrated, diluted with water and extracted thoroughly with chloroform. Evaporation of the chloroform leaves 1,2-diamino-4-(thiocyanatomethylthio)benzene.

A mixture of 2.6 g. of the above diamino compound, 2.6 g. of 1,3-bis(methoxycarbonyl)-S-methyl-isothiourea and 1 ml. of acetic acid is treated with 40 ml. of refluxing 50% aqueous ethanol for 4 hours. The cooled mixture is filtered yielding 5(6)-thiocyanatomethylthio-2-carbomethoxyaminobenzimidazole, which may be recrystallized from methanol-chloroform.

0.84 G. of 5(6)-thiocyanatomethylthio-2-carbomethoxyaminobenzimidazole is dissolved in a mixture of 50 ml. of chloroform and 10 ml. of acetic acid. The solution is treated at −30° to −20° C. with a solution of 0.62 g. of m-chloroperbenzoic acid in 15 ml. of chloroform, then allowed to warm slowly to room temperature. After 15 hours the solvent is removed under vacuum and the residue treated with dilute potassium bicarbonate solution. The crude 5(6)-thiocyanatomethylsulfinyl-2-carbomethoxyaminobenzimidazole is filtered off and recrystallized from methanol-chloroform.

In certain of the Examples above, specific reaction sequences have been extended, in a general sense, to the preparation of other similar and related compounds. It should be understood, however, that with respect to any compound which has been prepared by the extension of a specific reaction sequence, it may be necessary or desirable to utilize solvents, reaction media, recrystallization media, reaction times or temperatures, etc., other than the ones given in the specific reaction sequence upon which such extension is based. Additionally, the specific reaction sequence or manner in which particular compounds are to be prepared will depend, inter alia, upon the availability of the necessary starting materials, or the ease in which the desired starting materials can be prepared, and the reactivity thereof. These variations are deemed to be within the skill of those working in this art and will be apparent from a consideration of the particular reactants utilized and/or particular compound desired to be produced.

While the present invention has been described with reference to specific embodiments thereof, it should be understood by those skilled in this art that various changes may be made and equivalents may be substituted without departing from the true spirit and scope of the invention. In addition, many modifications may be made to adapt a particular situation, material or composition of matter, process, process step or steps, or then-present objective to the spirit of this invention without departing from its essential teachings.

What is claimed is:
1. A compound represented by the formula:

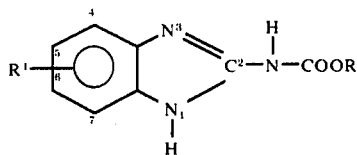

where R is a lower alkyl group having 1 to 4 carbon atoms; $R^1$ is $-SOR^2$, $-SO_2R^2$, $-SCN$, $-SR^5$, $-OR^5$, or $M'(CH_2)_nMR^7$ where M and M' are independently O, S,

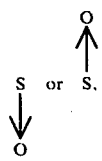

$R^7$ is lower alkyl having 1 to 4 carbon atoms, phenyl or naphthyl, and $n$ is 1–4; $R^2$ is lower alkyl having from 1 to 6 carbon atoms, cycloalkyl having 3 to 7 carbon atoms, lower alkenyl or lower alkynyl having 3 to 6 carbon atoms, benzyl, phenethyl, phenyl or naphthyl; and $R^5$ is lower alkenyl, lower alkynyl, or benzyl or phenethyl; the $R^1$ substitution being at the 5(6)-position; or a pharmaceutically acceptable salt thereof.

2. A compound represented by the formula:

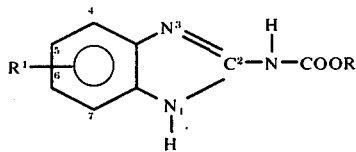

where R is a lower alkyl group having 1 to 4 carbon atoms; $R^1$ is $-SOR^2$ or $-SO_2R^2$, $R^2$ is lower alkyl having from 1 to 6 carbon atoms or cycloalkyl having 3 to 7 carbon atoms; said lower alkyl group of said $R^2$ substituent being optionally substituted with one or more alkoxy having 1 to 6 carbon atoms, phenyl, naphthyl, thiocyanato, benzoyl, naphthoyl hydroxy, cycloalkyl having 3 to 7 carbon atoms, halo, cyano, or nitro radicals; the $R^1$ substitution being at the 5(6)-position; or a pharmaceutically acceptable salt thereof.

3. The compound of claim 2 wherein $R^2$ is lower alkyl.

4. The compound of claim 2 wherein R is methyl.

5. The compound of claim 2 wherein said compound is 5(6)-methylsulfinyl-2-carbomethoxyaminobenzimidazole.

6. The compound of claim 2 wherein said compound is 5(6)-ethylsulfinyl-2-carbomethoxyaminobenzimidazole.

7. The compound of claim 2 wherein said compound is 5(6)-n-propylsulfinyl-2-carbomethoxyaminobenzimidazole.

8. The compound of claim 2 wherein said compound is 5(6)-i-propylsulfinyl-2-carbomethoxyaminobenzimidazole.

9. The compound of claim 2 wherein said compound is 5(6)-n-butylsulfinyl-2-carbomethoxyaminobenzimidazole.

10. The compound of claim 2 wherein said compound is 5(6)-trifluoromethylmethylsulfinyl-2-carbomethoxyaminobenzimidazole.

11. A compound represented by the formula:

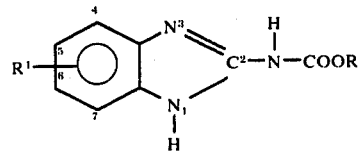

where R is lower alkyl group having 1 to 4 carbon atoms; $R^1$ is -SCN; the $R^1$ substitution being at the 5(6)-position; or a pharmaceutically acceptable salt thereof.

12. A compound represented by the formula:

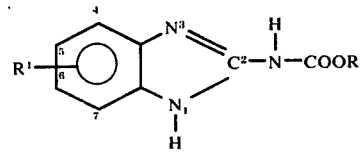

where R is a lower alkyl group having 1 to 4 carbon atoms; $R^1$ is $M'(CH_2)_nMR^7$ where M and M' are independently O, S, $R^7$ is lower alkyl having 1 to 4 carbon atoms, phenyl or naphthyl, and $n$ is 1–4; the $R^1$ substitution being at the 5(6)-position; or a pharmaceutically acceptable salt thereof.

13. The compound of claim 12 wherein said compound is 5(6)-methylsulfinylethylthio-2-carbomethoxyaminobenzimidazole.

14. The compound of claim 12 wherein said compound is 5(6)-methylsulfinylmethylthio-2-carbomethoxyaminobenzimidazole.

15. The compound of claim 12 wherein said compound is 5(6)-phenylsulfinylmethylthio-2-carbomethoxyaminobenzimidazole.

* * * * *